United States Patent
White et al.

(10) Patent No.: US 6,750,065 B1
(45) Date of Patent: Jun. 15, 2004

(54) IMMUNOASSAYS INVOLVING SURFACE ENHANCED RAMAN SCATTERING

(75) Inventors: Peter Cyril White, Glasgow (GB); Salah Athmani, Glasgow (GB); William Ewen Smith, Glasgow (GB); Daran Antony Sadler, Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

(21) Appl. No.: 09/623,033
(22) PCT Filed: Feb. 26, 1999
(86) PCT No.: PCT/GB99/00588
§ 371 (c)(1),
(2), (4) Date: Nov. 20, 2000
(87) PCT Pub. No.: WO99/44065
PCT Pub. Date: Sep. 2, 1999

(30) Foreign Application Priority Data

Feb. 26, 1998 (GB) .............................................. 9804083

(51) Int. Cl.⁷ ..................... G01N 33/543; G01N 33/58; G01N 33/94
(52) U.S. Cl. ..................... 436/518; 436/164; 436/173; 436/525; 436/801; 436/805; 436/536; 435/7.95; 435/6; 435/7.94
(58) Field of Search .............................. 435/7.95, 7.98, 435/6; 436/164, 173, 518, 525, 801, 805, 536, 541

(56) References Cited

U.S. PATENT DOCUMENTS 5,567,628 A * 10/1996 Tarcha et al. ............... 436/525
6,127,120 A * 10/2000 Graham et al. ................ 435/6

FOREIGN PATENT DOCUMENTS

| EP | 0 587 008 | 3/1994 |
|---|---|---|
| EP | 0 654 670 | 5/1995 |
| WO | WO 96/22531 | 7/1996 |
| WO | WO 97/05280 | 2/1997 |

OTHER PUBLICATIONS

Narang, U. et al. "A Displacement Flow Immunosensor for Explosive Detection Using Microcapillaries"; Analytical Chemistry, 69(14): 2779–2785 (1997).

Rubim, J.C. et al. "Surface–Enhanced Raman Scattering and Atomic Force Microscopy of Brass Electrodes in Sulfuric Acid Solution Containing Benzotriazole and Chloride Ion"; Applied Spectroscopy, 47(1): 80–84 (1993).

(List continued on next page.)

*Primary Examiner*—Long V. Le
*Assistant Examiner*—Jacob Cheu
(74) *Attorney, Agent, or Firm*—Dann, Dorfman, Herrell & Skillman, P.C.

(57) ABSTRACT

Immunoassay displacement methods for detecting (preferably identifying) the presence or amount of a target analyte (e.g. drug) in a sample comprising the steps of: (a) exposing the sample to a complex comprising an immobilized antibody capable of specifically binding the analyte, said antibody being specifically bound to a displacement agent, wherein said agent comprises: (I) an analyte analog capable of specifically binding the antibody, (ii) a surface enhanced resonance raman scattering (SERRS) or a surface enhanced raman scattering (SERS) active label, (iii) a SERRS or SERS surface-seeking group (e.g. benztriazole), whereby any analyte present in the sample causes the displacement of agent from the antibody; (b) exposing any displaced agent to a SERRS or SERS surface; and, (c) detecting any displaced agent associated with said surface using SERRS or SERS. In preferred forms of the invention several target analytes are detected from a single source or sample simultaneously. Also provided are agents per se e.g. for use in drug or explosive detection. These may include chromophores and linking groups.

32 Claims, 15 Drawing Sheets

TYPE A

TYPE B

TYPE C

OTHER PUBLICATIONS

Wilson, H. et al. "The Use of Deposited Sol to Detect Benzotriazole at a Non–SERS–Active Copper Surface"; Journal of Raman Spectrocopy, 25: 899–901 (1994).

Rodger, C. et al. "Surface–enhanced resonance–Raman scattering: an informative probe of surfaces"; Journal of the Chemical Society, Dalton Transactions, 791–799 (1996).

Rohr, T.E., et al. "Immunoassay Employing Surface–Enhanced Raman Spectroscopy"; Analytical Biochemistry, 182: 388–398 (1989).

Dou, X. et al. "Enzyme Immunoassay Utilizing Surface–Enhanced Raman Scattering of the Enzyme Reaction Product"; Analytical Chemistry, 69: 1492–1495 (1997).

Cabalin, L.M. et al. "Flow–injection analysis and liquid chromatography: surface–enhanced Raman spectrometry detection by using a windowless flow cell"; Analytica Chimica Acta, 318: 203–210 (1996).

* cited by examiner

Figure 1:
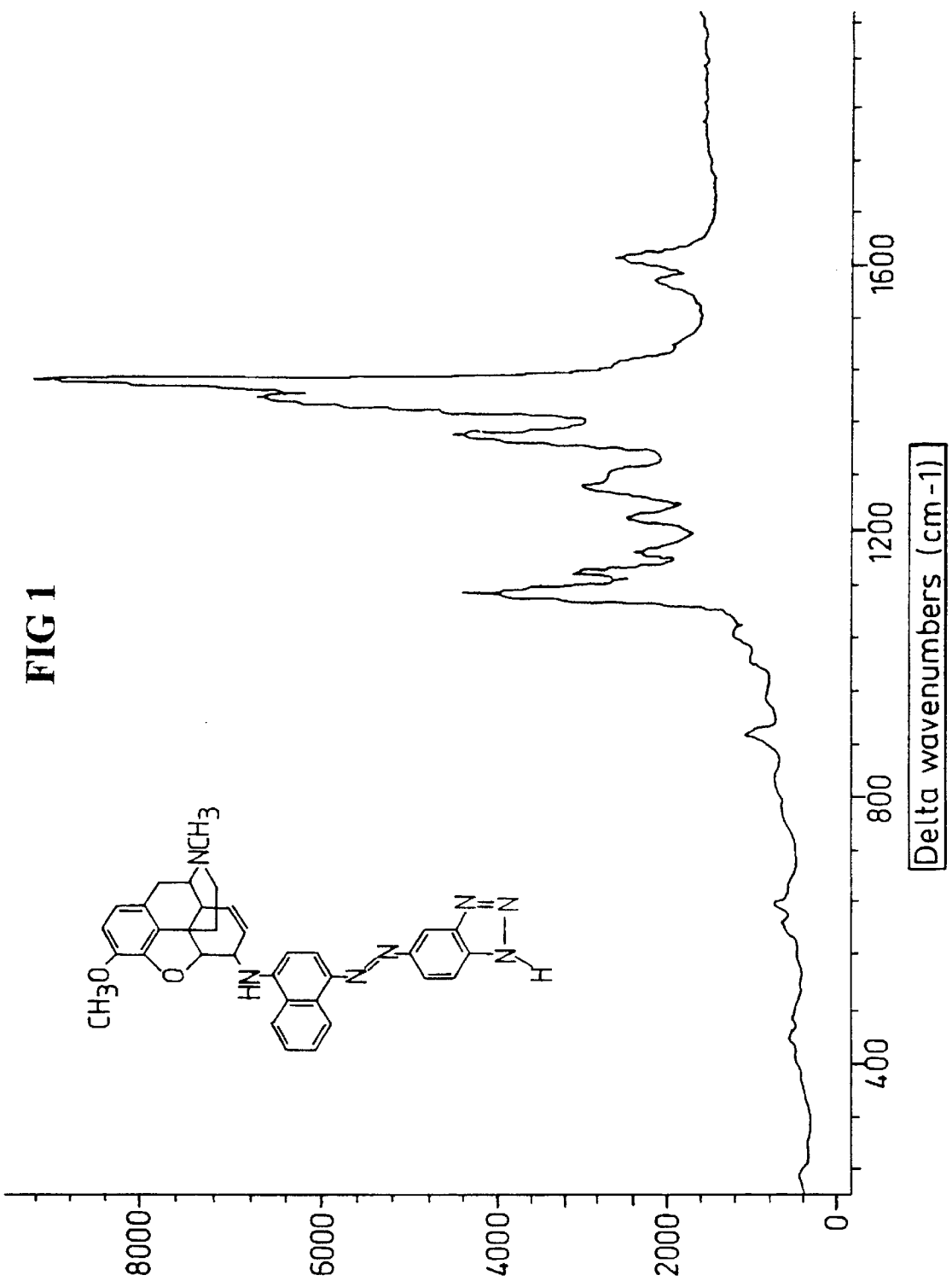

A1 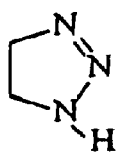
A2 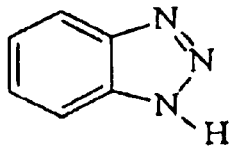
A3 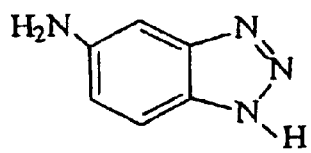
A4 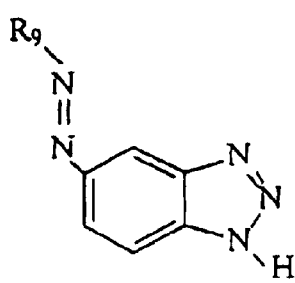
A7 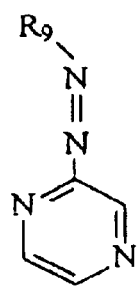
A8 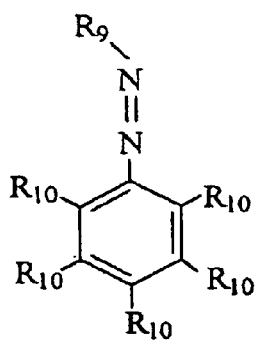
Where $R_{10}$ = $(CH_2)_n$ – COOH
$(CH_2)_n$ – $PPh_2$
$(CH_2)_n$ – SH
$(CH_2)_n$ – $NH_2$
$(CH_2)_n$ – OH
H
n = 0 – 4
A9 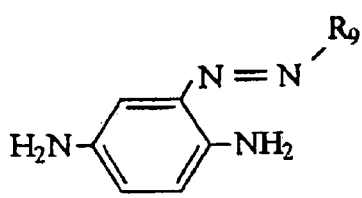
A10 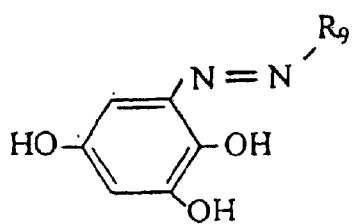
FIG 6A1

Figure 2:
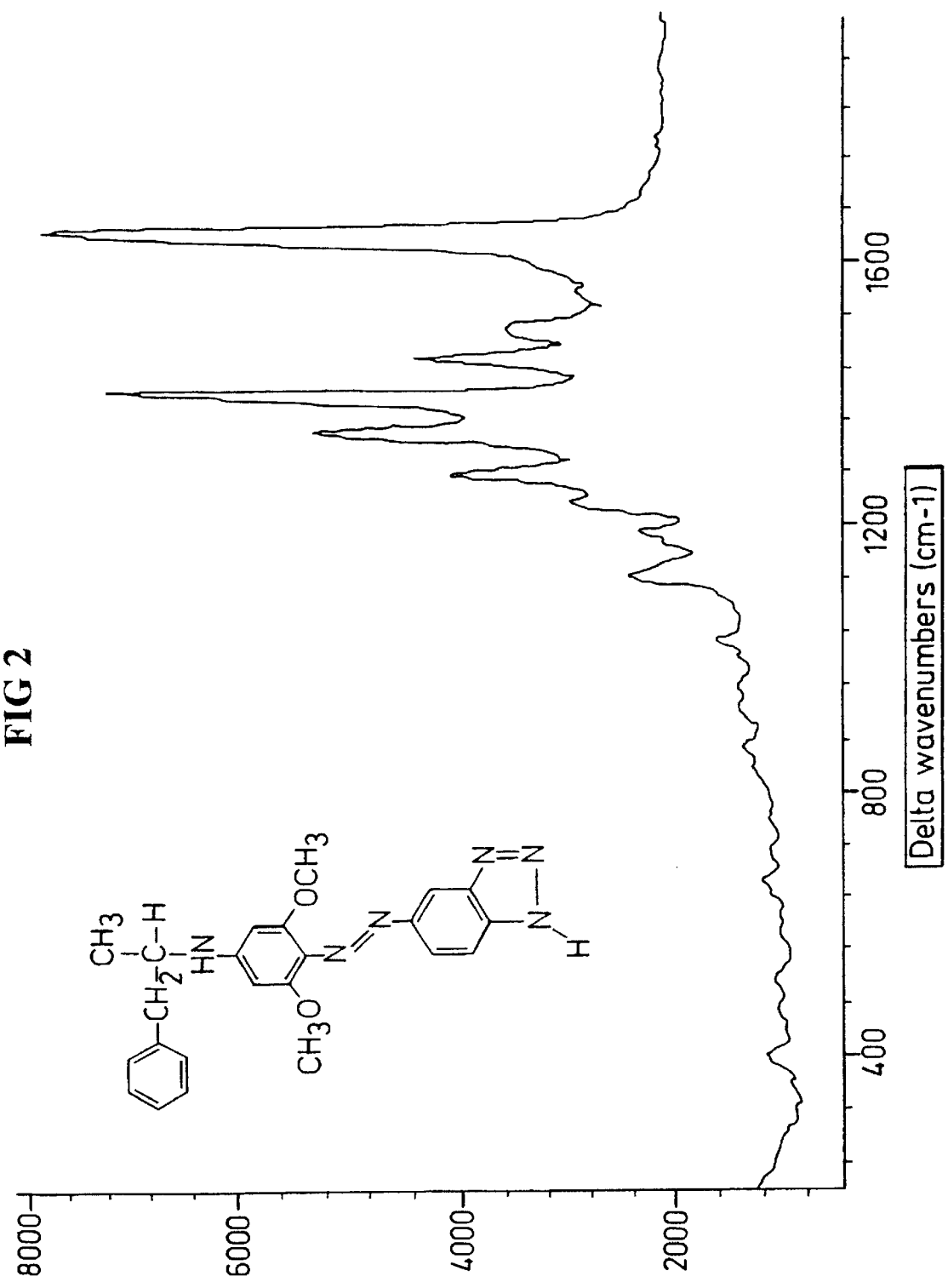

A 5 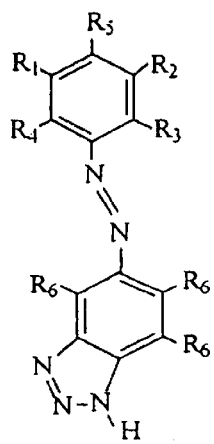 A 6 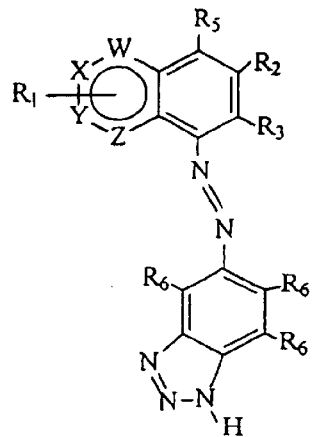
Where $R_1 - R_6$ =
- phenyl, naphthyl, pyridyl etc
- analyte
- CH=CHR
- $R-C\begin{smallmatrix}(CH_2)n\\|\\(CH_2)m\end{smallmatrix}$
- C=NR
- C=N⁺R | O⁻
- C(H)O
- C(R)O
- C(NHR)O
- CH₂NHR
- CH₂OR
- CH₂halogen
- N₃
- NO
- NO₂
- NHCONHR
- NHCSNHR
- NHCOR
- NHR
- OH
- OR
- SiR₃
- SH
- SR
- SSR
- SeR
- SnR₃
- PbR₃
- where R = H or any alkyl, aryl group
W,X,Y,Z = C,O,S or N
n,m = any integer > 1
FIG 6A2

Figure 3:
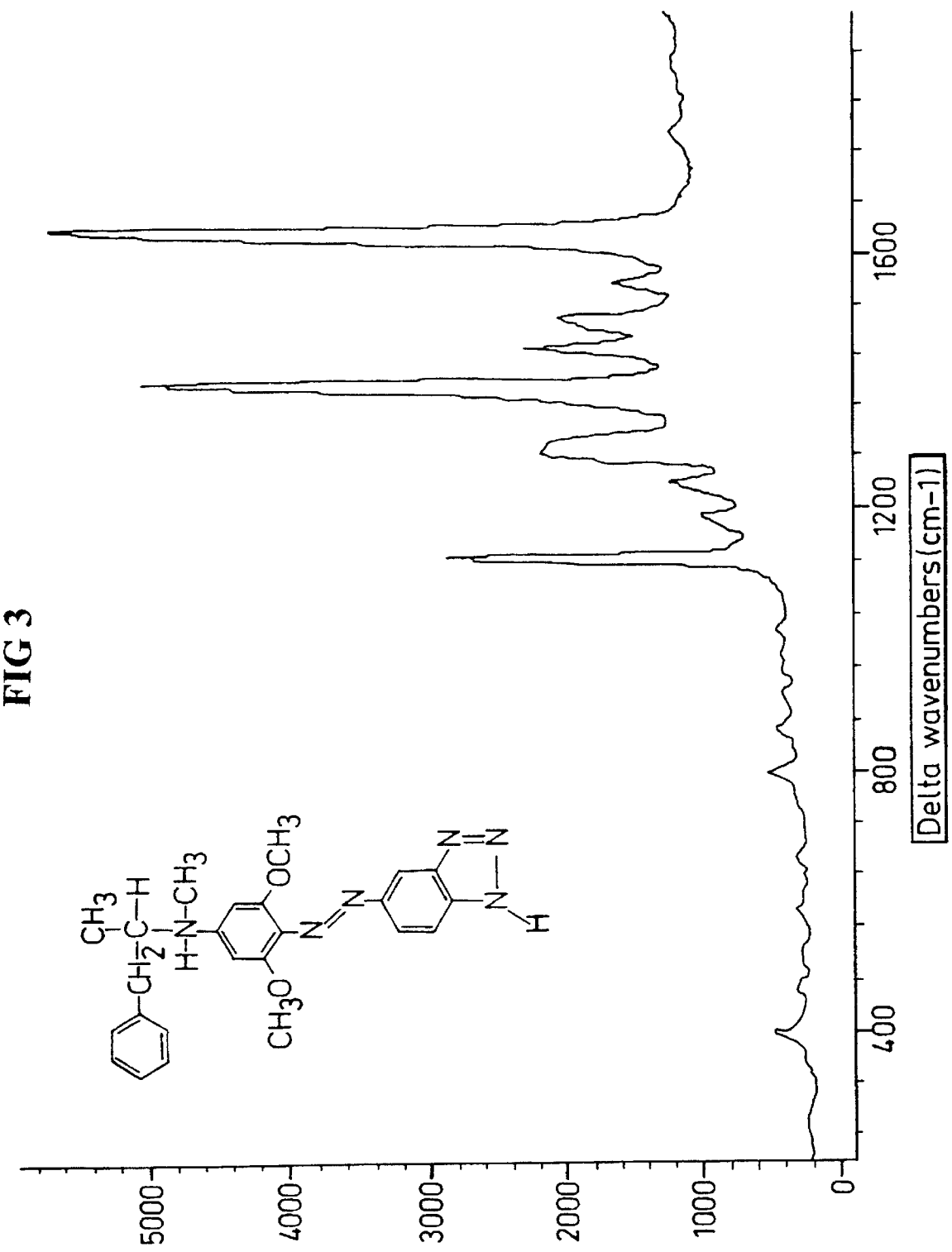

A 11 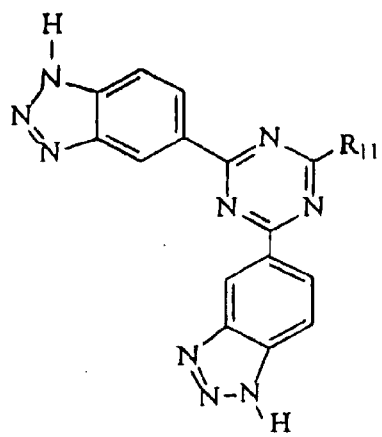
A 12 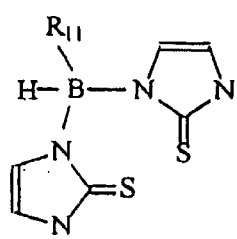
A13 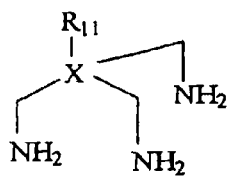
Where X = N or C
$R_{11}$ = —Ph—N═N— $R_9$
or — $CH_2$ —Ph—N═N— $R_9$
FIG 6A3

Figure 4:
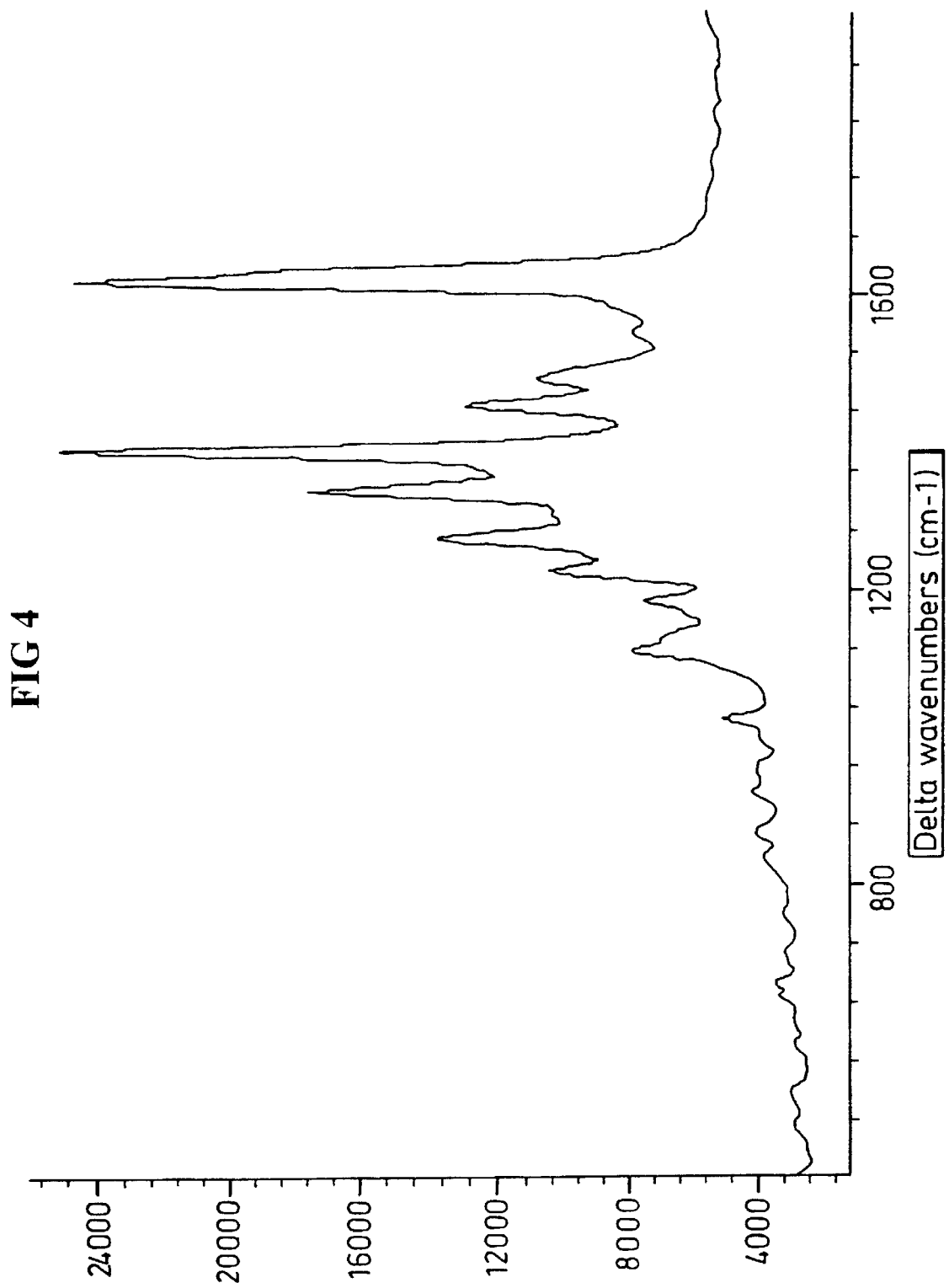

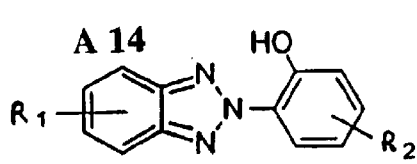
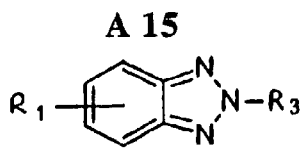
$R_1$ usually hydrogen    $R_2$ alkyl groups    $R_3$ alkyl or aryl esters
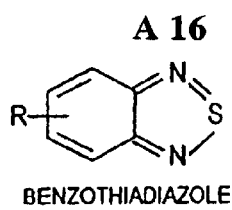
BENZOTHIADIAZOLE
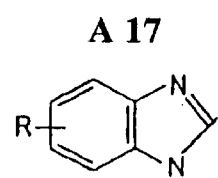
BENZIMIDAZOLE
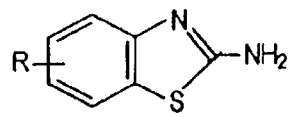
2-AMINO BENZOTHIAZOLE
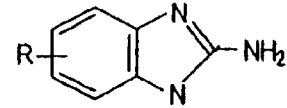
2-AMINOBENZIMIDAZOLE
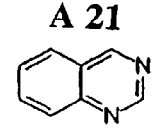
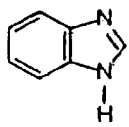
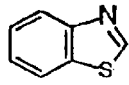
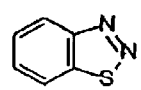
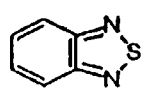
PYRIMIDINES    IMIDAZOLES    BENZOTHIAZOLES    BENZOTHIADIAZOLES
FIG 6A4

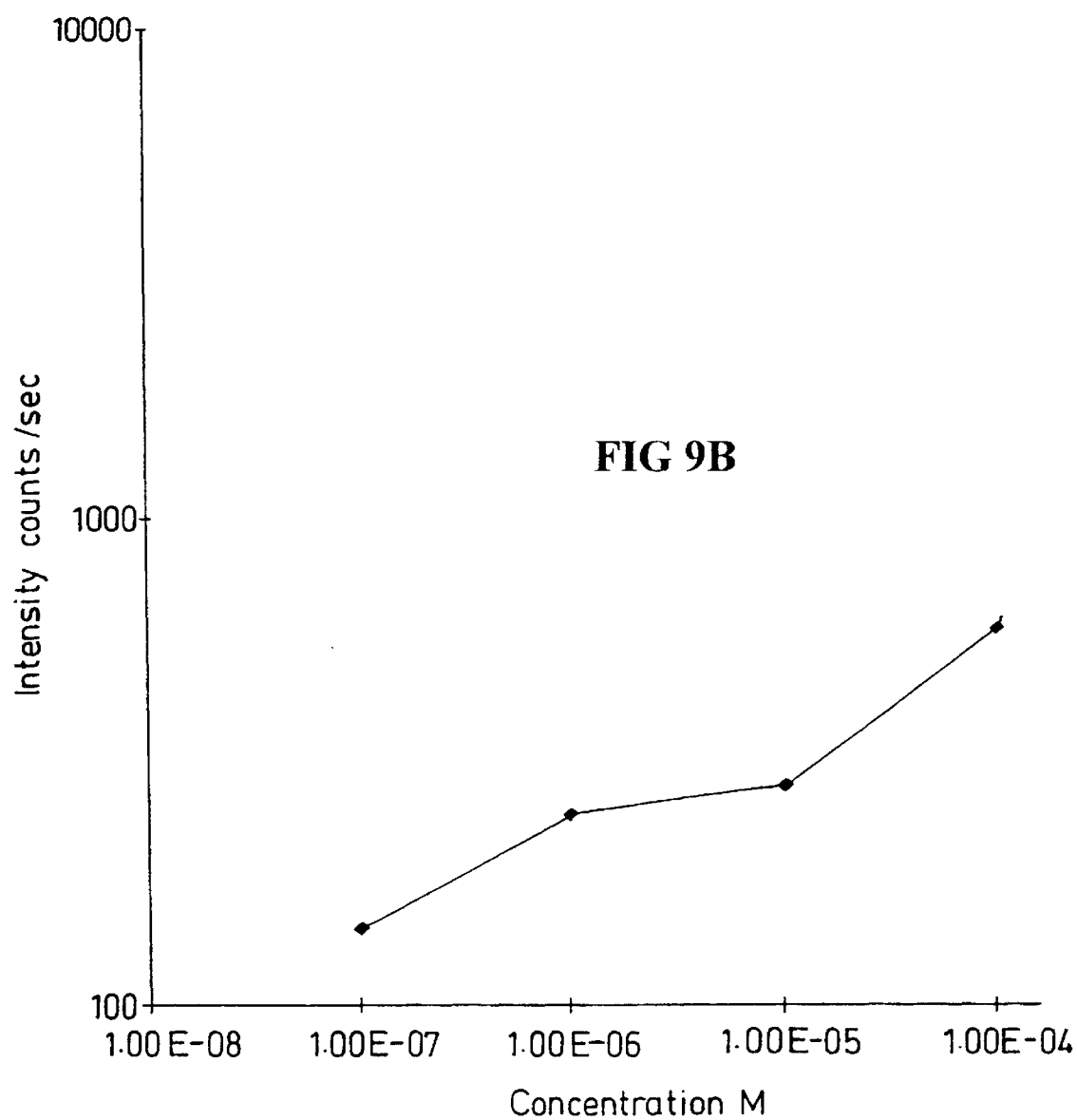

IMMUNOASSAYS INVOLVING SURFACE ENHANCED RAMAN SCATTERING

TECHNICAL FIELD

The present invention relates to methods and materials for assaying analytes using immunoassays and surface enhanced Raman scattering.

It further relates to methods of preparing materials for use in such assays, and kits and other equipment for performing such methods.

PRIOR ART

Surface enhanced Raman scattering

The invention provides a technique based on the principle of "surface enhanced Raman scattering" (SERS) and on a modification of that principle known as SERRS (surface enhanced resonance Raman scattering). These principles are already known and well documented, and have been used before in the detection and analysis of various target materials.

Briefly, a Raman spectrum arises because light incident on an analyte is scattered due to excitation of electrons in the analyte. "Raman" scattering occurs when an excited electron returns to an energy level other than that from which it came—this results in a change in wavelength of the scattered light and gives rise to a series of spectral lines at both higher and lower frequencies than that of the incident light. The scattered light can be detected orthogonally to the incident beam.

Normal Raman lines are relatively weak and Raman spectroscopy is therefore too insensitive, relative to other available detection methods, to be of use in chemical analysis. Raman spectroscopy is also unsuccessful for fluorescent materials, for which the broad fluorescence emission bands (also detected orthogonally to the incident light) tend to swamp the weaker Raman emissions.

However, a modified form of Raman spectroscopy, based on "surface-enhanced" Raman scattering (SERS), has proved to be more sensitive and hence of more general use. The analyte whose spectrum is being recorded is closely associated with a roughened metal surface. This leads to a large increase in detection sensitivity, the effect being more marked the closer the analyte sits to the "active" surface (the optimum position is in the first molecular layer around the surface, ie, within about 20 nm of the surface).

The theory of this surface enhancement is not yet fully understood, but it is thought that the higher valence electrons of the analyte associate with pools of electrons (known as "plasmons") in pits on the metal surface. When incident light excites the analyte electrons, the effect is transferred to the plasmons, which are much larger than the electron cloud surrounding the analyte, and this acts to enhance the output signal, often by a factor of more than $10^6$.

A further increase in sensitivity can be obtained by operating at the resonance frequency of the analyte (in this case usually a coloured dye attached to the target of interest, although certain target analytes themselves may have suitable colour characteristics to use with appropriate lasers). Use of a coherent light source, tuned to the absorbance maximum of the dye, gives rise to a $10^3$–$10^5$-fold increase in sensitivity. This is termed "resonance Raman scattering" spectroscopy.

When the surface enhancement effect and the resonance effect are combined, to give "surface enhanced resonance Raman scattering" or SERRS, the resultant increase in sensitivity and robustness is more than additive. Moreover, the sensitivity does not seem to depend so critically on the angle of orientation of the analyte to the surface, as is the case with SERS alone. A SERRS signal can be more easily discriminated from contamination and background and tends to be less variable with local conditions (e.g., ionic strength or pH when an analysis is carried out in solution). Fluorescence is also quenched, giving cleaner Raman spectra and allowing fluorescent dyes to be used as detectable analytes. Generally, the signal enhancement means that a much larger range of analytes may be usefully detected than using normal Raman spectroscopy. Furthermore, the enhancement means that a less powerful light source is required to excite the analyte molecules.

With SERRS, detection limits down to one molecule have been achieved for compounds which absorb light in the visible wavelength region or the electromagnetic spectrum (see Emory & Nie (1997) "Near-Field Surface-Enhanced Raman Spectroscopy on Single Silver Nanoparticles", Anal. Chem. 69: 2631–2635). This technique is therefore more sensitive than fluorescence (see e.g., C Rodger et al, *J. Chem. Soc. Dalton Trans.* (1996), pp791–799) and furthermore, the SERRS spectra obtained contain molecular information which permit compound identification and discrimination.

The present invention herein disclosed may be used in either a SERS or SERRS format, and the abbreviation SER(R)S is used hereinafter to demonstrate this. Generally speaking, owing to its sensitivity advantages, SERRS will be preferred. However the use of SERS, particularly with appropriate surface seeking groups, is also contemplated.

SE(R)RS in nucleic acid detection

WO 97/05280 (University of Strathclyde) discusses the use of SE(R)RS in nucleic acid detection and sequencing.

Immunoassays

EP 0 587 008 (Abbott) discusses the use of SE(R)RS immunoassays. Essentially they propose monitoring the formation of a "complex" comprising analyte, binding member (generally antibody), a SE(R)RS label, and a particulate surface. In other embodiments competitive assays are proposed wherein analyte and labelled-analyte-analog compete to form complexes which are then monitored. Complexes between specific binding members and surfaces are generally formed covalently or by direct absorption. A brief mention of multiple analyte detection is made, but no examples are given. Detection levels in the region of $\mu$g/ml are discussed in relation to single analytes (see e.g. Example 16 and FIG. 10).

The concept of using SE(R)RS for detecting certain analytes simultaneously has been discussed in the art generally (see C H Munro et al in *Analyst*, April 1995, 120, pp993–1003). This study used a variety of prepared samples to show that up to 20 RR-active dyes could be discriminated. The importance of controlled aggregation and purity of the samples was stressed, and in particular a purifying pretreatment step (such as TLC) was advocated.

DISCLOSURE OF THE INVENTION

The present inventors have now developed a novel SE(R)RS based immunoassay which is broadly based on the displacement of SE(R)RS active (generally labelled) analyte analogs which are modified such as to have particular SE(R)RS surface seeking properties. The use of modified analogs in a displacement format (rather than the labels and direct or competitive formats disclosed in the relevant art)

offers the potential for improved sensitivity and selectivity of detection, allowing robust quantitative detection of multiple analytes simultaneously from untreated 'real world' samples.

Displacement immunoassays, such as those using capillaries, have been disclosed in the art, but not in relation to SE(R)RS. For instance Narang et al (Anal.Chem.1997 69, 961–964 and 2779–2785) and Whelan (Anal.Chem.1993 65, 3581–3665) both used fluorescence detection.

The present inventors have discovered that one of the main problems in using SE(R)RS for quantitative analysis, particularly in an immunoassay displacement format, has been lack of control of the surface adsorption process of the label onto the SE(R)RS surface. Many ligands dynamically adsorb and desorb to surfaces other than the SE(R)RS surface, making it difficult to obtain usable (preferably linear) calibration graphs.

This difficulty was not appreciated in the prior art. The inventors have further provided a solution to this problem by the provision of attachment groups which can be used to give the SE(R)RS label a specific selectivity for SE(R)RS surfaces, thereby making quantitative determination of labelled ligands possible.

The surface seeking groups are soluble in solution but interact preferentially with the SE(R)RS surface, for instance by forming flexible polymeric structures on it, or by utilising flexible 'bolus' type structures i.e. which have a number of complexing groups flexibly arranged around a central core. These interactions may be achieved even under diverse environmental conditions, such as varied salt or protein concentrations, thereby permitting the quantitative analysis of untreated biological samples. In preferred embodiments the use of surface seeking groups permits positive identification of SER(R)S material displaced from bound antibody directly on the basis of its inherent analyte-related structure.

Also disclosed are particular methods and apparatus for carrying out the displacement assays of the present invention, as well as certain novel, preferred, methods for generating modified (as compared with those in the prior art) labelled analyte analogs and novel analogs per se. These and various other aspects of the present invention will now be discussed in more detail.

Thus in a first aspect of the present invention there is disclosed a method for detecting the presence or amount of a target analyte in a sample comprising the steps of:

(a) Exposing the sample to a complex comprising an immobilised antibody capable of specifically binding the analyte, said antibody being specifically bound to a displacement agent, wherein said agent comprises:
   (i) an analyte analog capable of specifically binding the antibody,
   (ii) a SE(R)RS active label,
   (iii) a SE(R)RS surface-seeking group,
whereby any analyte present in the sample causes the displacement of agent from the antibody;

(b) Exposing any displaced agent to a SE(R)RS surface; and, (c) Detecting any displaced agent associated with said surface.

By "target analyte" is meant any analyte which it is desired to detect or quantify. In this context "detect" means to establish that an analyte or class of analyte could be in a sample. Where circumstances require detection may be followed by positive identification using further confirmatory testing with complementary methods (e.g. GC/MS). Such circumstances may include analysis for legal prosecution purposes e.g., in drugs of abuse.

By "sample" may be anything which it is desired to test for analyte. It may or may not be pre-treated prior to carrying out the methods of the invention.

By "complex" is meant an immunocomplex whereby the antibody is specifically, non-covalently, bound to the displacement agent. As is well understood in the art, for specific binding, generally speaking, the antibody will have been raised, or derived from one which was raised, against the analyte, or an analog thereof, possibly in the form of a hapten-conjugate. "Specifically" expressly includes the situation of cross-reactive antibodies i.e. those which bind two or more compounds which have the same or similar stereochemical configurations (comprise the same or similar epitopes).

By "antibody" is meant any antibody, or fragment or derivative of an antibody variable region, which is capable of specific binding to analyte and agent as described above. The antibody is "immobilised" by associating it with a solid phase such that it can not interfere with the detection of displaced agent during the assay.

The "displacement agent" of the present invention has three important aspects:

Firstly it must share sufficient structural identity with the analyte to permit specific binding to the same antibody.

Secondly it must be SE(R)RS active i.e. capable of generating a SE(R)RS spectrum. It should be noted that the term "SE(R)RS active label" is used herein (unless context demands otherwise) to denote that the agent as a whole is SERRS or SERS active, possibly by virtue of the structure of the analyte analog or surface-seeking group, and does not necessarily imply a particular separate label portion.

Thirdly it must have a SE(R)RS surface-seeking group. This is a group which is readily adsorbed on a suitable SE(R)RS surface in a selective manner, as discussed above. The adsorption may be of sufficient strength that the agent is effectively immobilised on to that surface at levels up to monolayer coverage.

In preferred forms of the invention, as described below, the method is used to positively "identify" the analyte in the sample. By ensuring that the SERRS spectrum of the detected entity in the assay (i.e. the displacement agent) has a contribution from the analyte-analog portion, the SERRS spectrum itself can be used to inherently "identify" the analyte-analog and hence the analyte, thus increasing the confidence in the result and therefore reducing the need for confirmatory screening. Work done by the present inventors has shown that a SE(R)RS contribution from the analyte-analog is most readily achieved by ensuring that the analyte-analog is brought into close proximity to the SE(R)RS surface by careful combination with the surface seeking group and other components of the displacement agent. Such an approach (in which the inherent characteristics of the analyte analog are, in effect, used to provide a specific detectable label by bringing it into sufficient proximity to the SER(R)S surface) has not previously been proposed for immunoassays, nor would it have apparently been compatible with the kind of formats and molecules discussed in e.g. EP 0 587 008.

The amount of agent displaced from the immunocomplex on exposure to analyte will depend on a number of factors, including the relative affinities of the agent and analyte for the antibody (which is generally constant under particular conditions), and the concentration of analyte present (which forms the basis for the assay). It can thus be seen that being able to accurately and reproducibly determine the amount of displaced agent is crucial to making a confident, quantitative assessment of the initial analyte concentration.

The exposure of the displaced agent to the SE(R)RS surface can take any form which bring the two into contact, in particular in such a way that non-displaced agent which is still part of the original immunocomplex does not interfere with the detection.

By 'SE(R)RS surface' is meant any suitable surface, usually metallic, which gives rise to enhancement of the Raman effect, of which many are known from the SER(R)S literature. It may for instance be an etched or otherwise roughened metallic surface, a metal sol or, more preferably, an aggregation of metal colloid particles. Silver, gold or copper surfaces, especially silver, are particularly preferred for use in the present invention and again, aggregated colloid surfaces are believed to provide the best SE(R)RS effect.

The detection of the displaced agent on the SE(R)RS surface can be conventional. By way of example, however, the following might apply to the spectroscopic measurements: typically, the methods of the invention will be carried out using incident light from a laser, having a frequency in the visible spectrum (the exact frequency chosen will depend on the label if present, surface and target in each case—frequencies in the red area of the visible spectrum tend, on the whole, to give rise to better surface enhancement effects). However, it is possible to envisage situations in which other frequencies, for instance in the ultraviolet or the near-infrared ranges, might be used. The selection and, if necessary, tuning of an appropriate light source, with an appropriate frequency and power, will be well within the capabilities of one of ordinary skill in the art, particularly on referring to the available SE(R)RS literature. To achieve highly sensitive detection, using SE(R)RS, a coherent light source is needed with a frequency at or close to the absorption maximum for the agent (as described above) or that of the surface plasmons. If lower sensitivities are required, the light source need not be coherent or of high intensity and so lamps may be used in combination with a monochromator grating or prism to select an appropriate excitation frequency; here, there is no need to operate at the resonant frequency of the agent or the plasmons. Various options are discussed, for instance, in WO 97/05280 (University of Strathclyde).

Preferred embodiments of the various aspects of the invention are as follows.

Analytes and samples

There are many occasions where screening for (detection and/or identification and quantification) of targeted analytes, often present at trace levels in samples, are required. These include clinical applications; the detection of drugs of abuse in illicit samples, body fluids and breath samples; explosives, pesticides, chlorophenols and other pollutants in soils, water, air, plants and other matrices. Ideally, in-situ methods (i.e. those not requiring any separation of the analytes from the sample prior to either their analysis or detection) are preferable. Increasingly, there also many instances where it is preferable to use analytical techniques which can be used in the field and therefore robust, portable and relatively inexpensive kits or instruments are required, such as those which may be based on the methods of the present invention.

Most preferably the analytes are selected form the following list:

(i) Drugs of abuse screening where a particular class or classes of drugs are in powder, liquid or gas form. The invention thus provides an alternative to the methods disclosed in U.S. Pat. No. 5,183,740 (Ligler et al) which uses displacement immunosensors monitored fluorometrically. Screening for such compounds is becoming of increasing importance, for instance in the field of competitive sports or law enforcement. Particular examples include amphetamines, opiates, benzodiazepines, barbiturates, cannabinoids, cocaine, LSD and their metabolites.

(ii) Screening for and identification of explosives. These include nitro-glycerine and nitrotoluenes including TNT, RDX, PETN and HMX.

(iii) Environmental pollutants or other indicators e.g., chlorophenols, explosives, rodenticides, herbicides etc., in liquids, air soils, plants, biological materials and other matrices.

(iv) Pharmaceuticals and their metabolites, or other therapeutic agents, such as may be detected in clinical analysis e.g. dopamine, ephedrine.

These analytes will frequently be present at very low concentrations in the sample e.g. sub ng/ml concentrations. This equates to $10^{-12}$ M for low molecular weight compounds. The Examples below show yet lower detection levels e.g. $10^{-16}$ M.

In preferred forms of the invention, multiple target analytes are detected from a single source or sample simultaneously. The Examples below show such simultaneous detection. This can be achieved by the use of multiple antibodies, each specific to the target analytes or classes of analytes. Also required are agents having different SE(R)RS active labels or chromophores with different chemical structures. Optionally the SE(R)RS signature of a single type of chromophore group (e.g. azo group) is modified by the nature of the agent of which it forms a part. The SE(R)RS active agents can thus give molecularly specific signals from which a computer program can identify agents (and hence the target analytes) in a mixture without separation.

Suitable discriminatable SE(R)RS labels are discussed hereinafter. Preferably up to 3, 5, 10 or 20 different displaced agents are associated with a SE(R)RS surface and detected in a single step. Higher numbers may also be detected under certain circumstances, in particular by selecting appropriate SE(R)RS labels and using advanced data discrimination methods and algorithms.

Thus, for instance, in roadside or other drug analysis, samples (e.g. saliva, breath, sweat, urine, blood etc.) may contain a whole range of metabolites at low concentration, and this may cause difficulties in detecting and discriminating different drug classes using conventional methods. The use of discriminatory antibodies and distinctive surface-seeking SE(R)RS agents, can be used to assess the presence of a number of these metabolites in a single exercise, for instance using the capillary-displacement apparatus described below.

The antibodies

As discussed above the antibodies used will be specific for (reactive or cross-reactive with) both the analyte and its corresponding agent. In certain embodiments the antibody may be specific for a class of analytes i.e. a 'broad specificity antibody', for instance as produced by methods disclosed in (or analogous to) PCT publications WO 94/27149 or WO 97/05170, both of the Minister of Agriculture, Fisheries and Food.

In such cases the agent specifically bound by the antibody will be displaced by a sample containing any one or more of the multiple compounds for which the antibody is specific. The subsequent detection of this agent will thus indicate the presence of any one or more of a class of compounds.

The antibody may be monoclonal or polyclonal. It may also be derived from a monoclonal antibody by expressing all or part of the nucleic acid encoding therefore in a suitable host cell such as to produce a polypeptide comprising all or part of the antigen binding site of the original antibody. Such antibodies and derivatives can be raised using any techniques commonly used in the immunology art (see e.g. Roitt et al in "Immunology 5th edition"—Pub. 1997 by Moseby International Ltd, London).

Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of Chimaeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the Vl and VH domains of a single antibody; (iv) the dAb fragment (Ward, E. S. et al., Nature 341, 544–546 (1989) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P Holliger et al Proc. Natl. Acad. Sci. USA 90 6444–6448, 1993).

Suitable antibodies, having the required (cross) specificity, can be selected for instance using affinity chromatography, or differential affinity chromatography where antibody samples are exposed to a series of different immobilised antigens in order to select those which have the desired binding properties. Such techniques are commonplace in the art.

In certain circumstances the use of agents based on different, related compounds may enhance sensitivity in that any analyte in the sample will bind to the antibody with higher affinity than the agent, thereby favouring displacement of agent.

Cross-specificity can also be utilised when detecting analytes for which appropriate labelled analogs can not readily be devised. In such instances, as described in more detail below, the displacement agent can be based on a similar (second) compound from the same class which binds to an antibody specific for the first.

In instances where the second compound is itself also being detected in the displacement assay (i.e is itself a distinct analyte) it is necessary that the displacement agent which is bound to the antibody specific for that second analyte is distinguishable from that which is bound to the antibody specific for the first.

An example of this approach is using an immunoassay for RDX and trinitrotoluene (TNT). Although TNT can be readily labelled With a SE(R)RS active dye, there is considerable complexity involved in trying to couple a SE(R)RS active label to RDX.

It is known that antibodies raised against TNT are frequently cross specific for other nitrated explosives e.g., RDX (Cyclotrimethylene trinitramine) and vice versa. By using this cross reactivity, SE(R)RS can be used indirectly with a labelled TNT molecule for the detection of RDX.

A SE(R)RS displacement immunoassay for detecting RDX and or TNT for example is achieved as follows. The antibodies for TNT and RDX which have cross reactivities to each other and other nitrated explosives are immobilised on beads or the inner surfaces of separate capillary tubes. Two different SE(R)RS active labels of TNT are then used to saturate the immobilised antibodies with one TNT label (TNT A) being used for the TNT antibodies and the other (TNT B) for the RDX antibodies. On passing a sample containing TNT and RDX through the system the TNT displaces the TNT A label from the TNT antibodies and the RDX displaces the TNT B label from the RDX antibodies. Hence since the TNT A and TNT B labels give different SE(R)RS spectra it is possible to detect both the RDX and TNT in the sample.

This approach can be used in static and continuous flow immunoassays (as described below) and the reason why RDX can be detected by this method is because of preferential analyte-antibody binding. RDX displaces the TNT B label from the RDX antibodies in preference to TNT because of the more favourable binding of RDX to the RDX antibodies. By increasing the number of SE(R)RS active labelled TNT compounds and antibody types this technique can be used to detect and identify several explosives in a mixture. It can also be used for other classes of analytes.

SE(R)RS surface

The displaced agents are detected on SE(R)RS surface.

The SE(R)RS surface may be provided by a naked metal or may comprise a metal oxide layer on a metal surface. It may include an organic coating such as of citrate or of a suitable polymer, such as polylysine or polyphenol, to increase its sorptive capacity.

Where the surface is colloidal, the colloid particles are preferably aggregated in a controlled manner so as to be of a uniform and desired size and shape and as stable as possible against self-aggregation. Processes for preparing such unaggregated colloids are already known. They involve, for instance, the reduction of a metal salt (e.g. silver nitrate) with a reducing agent such as citrate, to form a stable microcrystalline suspension (see P C Lee & D Meisel, *J. Phys. Chem.* (1982), 86, p3391). This "stock" suspension is then aggregated immediately prior to use. Suitable aggregating agents include acids (e.g., $HNO_3$ or ascorbic acid), polyamines (e.g., polylysine, spermine, spermidine, 1,4-diaminopiperazine, diethylenetriamine, N-(2-aminoethyl)-1, 3-propanediamine, triethylenetetramine and tetraethylenepentamine) and inorganic activating ions such as $Cl^-$, $I^-$, $Na^+$ or $Mg^{2+}$. To increase control over the process, all equipment used should be scrupulously clean, and reagents should be of a high grade. Since the aggregated colloids are relatively unstable to precipitation, they are ideally formed in situ in the detection sample and the SE(R)RS spectrum obtained shortly afterwards (preferably within about 15 minutes of aggregation).

The colloid particles are preferably monodisperse in nature and can be of any size so long as they give rise to a SE(R)RS effect—generally they will be about 4–80 nm in diameter, preferably 25–36 nm, though this will depend on the type of metal.

Preferably, the surface comprises silver colloid particles, which are preferably substantially hexagonal in shape and of about 20–36 nm maximum diameter.

Surface coating

When high levels of sensitivity are needed, as is the case when testing multiple, highly dilute, analytes simultaneously the quality of the active surface becomes more important than in many prior art techniques. Thus for a colloidal surface, for instance, the aggregated colloid particles should be of an optimum (and uniform) size and shape to enhance reproducibility and calibration. The use of a polyamine such as poly(L-lysine) assists in achieving this. This can help to control aggregation of colloid if present, and to enhance the interaction between the surface seeking group and the SE(R)RS surface.

The use of such polyamines is now well known to those skilled in the art, see for instance the discussion in WO 97/05280 (University of Strathclyde).

The polyamine may be a short-chain aliphatic polyamine such as spermine, spermidine, 1,4-diaminopiperazine, diethylenetriamine, N-(2-aminoethyl)-1,3-propanediamine, triethylenetetramine and tetraethylenepentamine; spermine and spermidine, in particular spermine with its four $NH_2$ groups per repeat unit, may be advantageous for use in the present invention. The polyamine is preferably introduced in the form of an acid salt such as its hydrochloride. As described above, it is of most use when the SE(R)RS-active surface is colloidal.

Preferably the surface coating agent (aggregating agent) is poly(L-lysine)

The polyamine should be introduced at a time which allows its interaction with the surface and/or displaced agent before the SER(R)S spectrum is obtained.

The amount of polyamine added is preferably of the order of 100 to 1000 times more than would be needed to obtain a monolayer coverage of the surface with the polyamine. In the case of a colloidal surface, this can be calculated with reference to the size of the colloid particles.

Detection & data analysis

In SE(R)RS the primary measurements are of the intensity of the scattered light and the wavelengths of the emissions. Neither the angle of the incident beam nor the position of the detector is critical. With flat surfaces an incident laser beam is often positioned to strike the surface at an angle of 60° with detection at either 90° or 180° to the incident beam. With colloidal suspensions detection can be at any angle to the incident beam, 90° again often being employed.

The intensity of the Raman signals needs to be measured against an intense background from the excitation beam, and for this reason the use of Raman agents with large Stokes' shifts is an advantage. The background is primarily Raleigh scattered light and specular reflection, which can be selectively removed with high efficiency optical filters.

Several devices are suitable for collecting SE(R)RS signals, including wavelength selective mirrors, holographic optical elements for scattered light detection and fibre-optic waveguides. The intensity of a SE(R)RS signal can be measured using a charge coupled device (CCD), a silicon photodiode, or photomultiplier tubes arranged either singly or in series for cascade amplification of the signal. Photon counting electronics can be used for sensitive detection. The choice of detector will largely depend on the sensitivity of detection required to carry out a particular assay.

Note that the methods of the invention may involve either obtaining a full SE(R)RS spectrum across a range of wavelengths, or selecting a peak and scanning only at the wavelength of that peak (ie, Raman "imaging").

Data processor

For multiple, different analytes, a complex SE(R)RS spectrum across a range of wavelengths will be obtained. Although analysis by eye may be possible, methods for obtaining and/or analysing a SE(R)RS spectrum will preferably include the use of some form of data processor such as a computer.

Raman signals consist of a series of discrete spectral lines of varying intensity. The frequencies and the relative intensities of the lines are specific to the label being detected and the Raman signal is therefore a "fingerprint" of the label. If a SE(R)RS analyzer is being used selectively to detect one or more agents out of a mixture then it will be necessary to detect the entire "fingerprint" spectrum for identification purposes. However if the analyzer is being used to quantitate the detection of one or several labels, each of which has a unique spectral line, then it will only be necessary to detect signal intensity at a chosen spectral line frequency or frequencies.

Once the SE(R)RS signal has been captured by an appropriate detector, its frequency and intensity data will typically be passed to a computer for analysis. Either the fingerprint Raman spectrum will be compared to reference spectra to confirm detection of the detected Raman active compound or the signal intensity at the measured frequencies will be used to calculate the amount of Raman active compound detected.

Displacement formats

As described above, the present invention is based on displacement methods.

These can be performed by method analogous to those discussed in Narang et al (Anal.Chem.1997 69, 961–964 and 2779–2785) and Whelan (Anal.Chem.1993 65, 3581–3665), or U.S. Pat. No. 5,183,740 (Ligler et al).

Briefly, in these formats the antibody is immobilized on a solid surface and then saturated with the labelled agent. On addition of a sample, which contains the analyte, some of the labelled agent will be displaced from the antibody. The detection of the labelled agent indicates the likely presence of the analyte in the sample and the size of the signal is proportional to the amount of analyte in the sample.

In preferred forms the antibodies can be immobilized on particles or other surfaces or either glass or plastic (e.g. polypropylene). If immobilized on flat surfaces parallel to each other or in a tube, the system can be used as either a static or continuous flow immunosensor.

For a continuous flow immunosensor, the labelled analytes are displaced from the antibodies into a flow of an aqueous solution and mixed with a silver colloid and aggregating agent before passing through a flow cell which is situated at the focal point of the laser beam in the Raman spectrometer. Raman spectra are then taken of the solution as it passes through the flowcell ie., continuous flow.

Alternatively, spectra are taken under stop-flow conditions or on fractions of the eluate that have been collected (cf. P W Atkins "Physical Chemistry 3rd Edition" at page 730, Pub. Oxford (1986)).

Preferably, a capillary based method is used, the system being broadly analogous to those used in the art with fluorescence detection.

For the simultaneous detection of multiple analytes, it is preferred that the continuous flow displacement immunoassay method is carried out by pumping the sample through two or more capillary tubes linked together in series.

Naturally parallel plates or other structures defining a flow channel can be immobilised with antibodies and used as an alternative to capillary tubes. Once again these can be utilised in series.

Analogous methods may be used for dealing witn air samples and solid samples. For instance solids can be solubilised. Gaseous samples can be adsorbed, and then desorbed into a solvent to provide a solution.

A simpler static version of this displacement technique is also possible. This may employ antibodies immobilised on beads, or on a surface of microtitre plate or other well or container. These are saturated with agent and exposed to analyte. The displaced agent is then detected in isolation, for instance by imaging a part of the system in which the antibodies or SER(R)S surface is not present. In one preferred form this embodiment uses magnetic beads treated with antibodies specific to the targeted analytes which, after being saturated with the appropriate SE(R)RS agent, are mixed with an aliquot of the sample in a small tube. The beads are drawn to the bottom of the sampling tube and after addition of the silver colloid and aggregating reagent a SE(R)RS spectrum of the labelled analytes is obtained. This static version can be used for single or multianalyte detection as with the continuous system.

Displacement agents

As described above, the agents of the present invention have three important aspects:

1. Structural Identity

Firstly the agent must share sufficient structural identity with the analyte to permit specific binding to the same antibody. Generally the agent will itself be derived from the analyte, but may incorporate one or more additional structural motifs or elements in order to render it SE(R)RS active and surface seeking. As already alluded to, in certain circumstances the agent may be based on compound which is related to (in the same class as) the analyte, and which is cross-reactive with an antibody raised to that analyte.

2. SE(R)RS Activity and Specificity of the Agent

Secondly it must be SE(R)RS active i.e. capable of generating a SE(R)RS spectrum.

Choice of SE(R)RS active group

If the analyte is non-UV absorbing, then an appropriate dye-label can optionally be incorporated into the agent analyte so that it is SE(R)RS active when illuminated with a visible wavelength laser. In certain circumstances the analyte-analog, or surface seeking group, may itself be "coloured" thereby obviating the need for a separate dye label, and in other cases the resonance enhancement may simply be foregone in order to simplify the production of the agent. If required, the tagging of a compound with a SE(R) RS active label may be achieved by derivatization of the compound (see Example 1, FIG. 6B).

Many SE(R)RS-active labels are already known and referred to in SE(R)RS literature. They include species containing chromophores and/or fluorophores which can be detected relatively easily using SE(R)RS.

Examples of suitable SE(R)RS-active species include fluorescein dyes, such as 5- (and 6-)carboxy-4',5'-dichloro-2',7'-dimethoxy fluorescein, 5-carboxy-2',4',5',7'-tetrachlorofluorescein and 5-carboxyfluorescein; rhodamine dyes such as 5- (and 6-)carboxy rhodamine, 6-carboxytetramethyl rhodamine and 6-carboxyrhodamine X; phthalocyanines such as methyl, nitrosyl, sulphonyl and amino phthalocyanines; azo dyes such as those listed in C H Munro et al, *Analyst* (1995), 120, p993; azomethines; cyanines and xanthines such as the methyl, nitro, sulphano and amino derivatives; and succinylfluoresceins. Each of these may be substituted in any conventional manner, giving rise to a large number of useful labels. The choice of label in any given case will depend on factors such as the resonance frequency of the label, the other species present, label availability, etc.

Most preferred is the azo group.

Combining the analyte analog and the SE(R)RS label.

Preferred SE(R)RS-active labels are those which possess appropriate functional groups to allow their easy attachment both to the analyte (or analog) and the surface seeking species. The label should preferably not contain groups likely to interfere with the binding of the agent to the antibody, or the SE(R)RS surface.

Derivitisation of existing analytes is discussed in general terms in U.S. Pat. No. 5,266,498 (Tarcha et al).

Figure 6B:
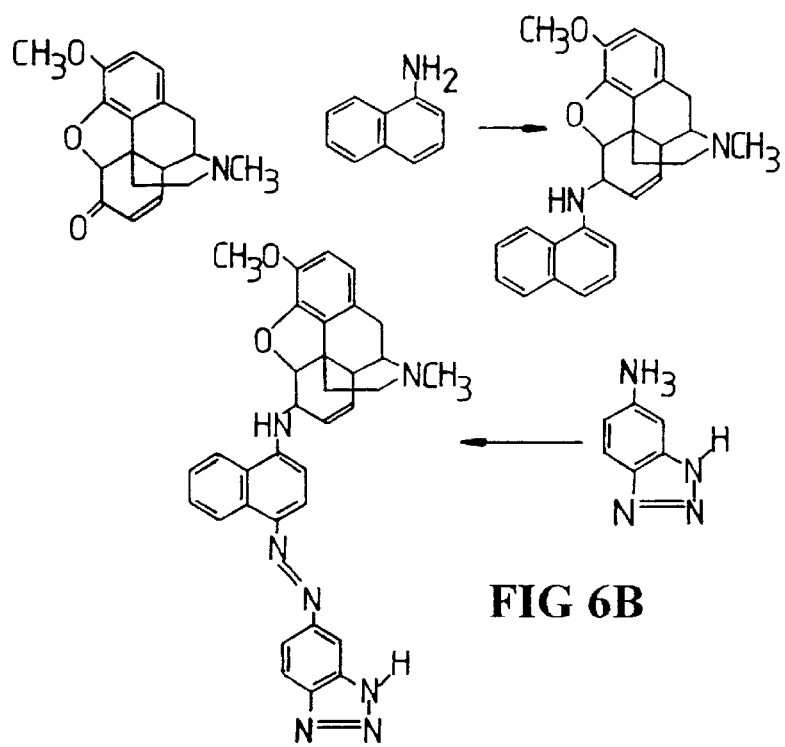
Figure 6C:
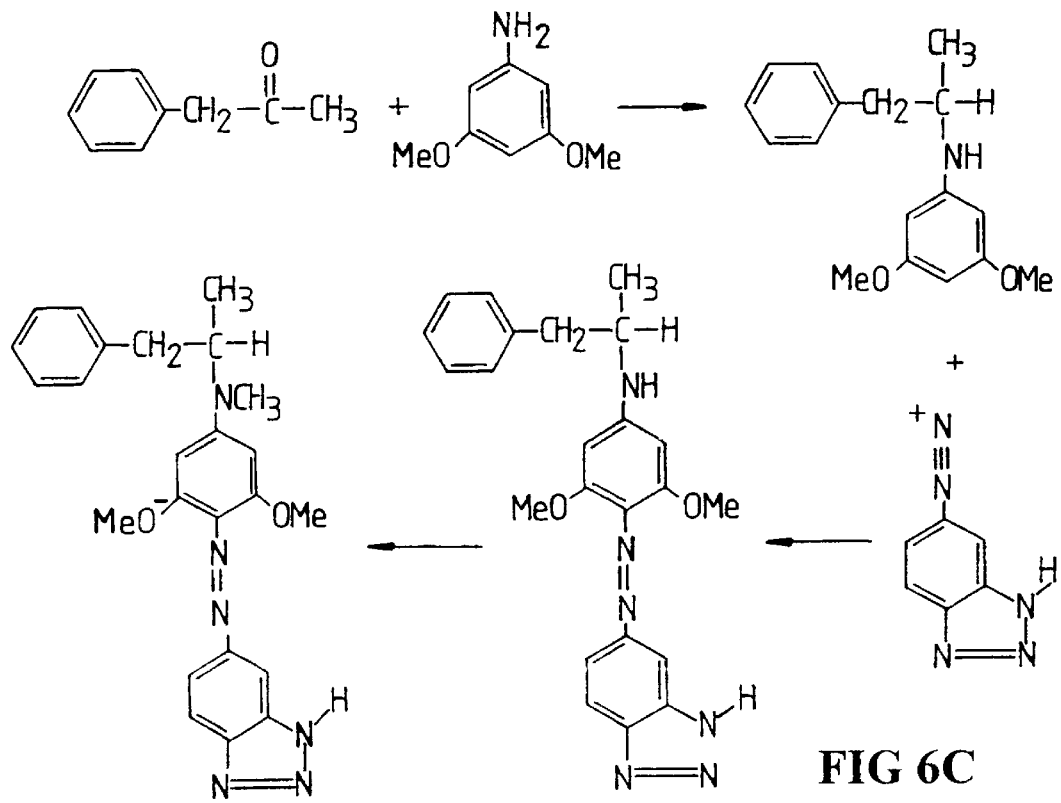

A novel alternative approach employs a mechanisms wherein the analyte to be labelled is not one of the starting materials but is produced in the synthesis of the labelled analyte, as exemplified with the synthesis azobenzotriazole labelled amphetamine and methylamphetamine (see Example 2 and 3, FIG. 6C).

Linking or other additional groups

Generally speaking it may be preferable to have a linking group between the analyte analog, and the other portion of the agent comprising the SER(R)S dye and the surface seeking group. There is no particular limitation on the nature of this linker, other than that it must be able to readily be joined to the other portions of the agent. It may also be advantageous to incorporate groups into the displacement agent which alter the resonance frequency of the label if present. These groups may be linker groups as described above, or may be substituents of other parts of the agent. Hereinafter the term "linker" or "linking" groups is used to describe all of these possibilities.

Thus the linking group can be a functionalised chemical group e.g. a substituted benzyl derivative such as dimethoxyaniline.

In another approach, the linking group can be an antibody. This has the SER(R)S dye and the surface seeking group derivitised to it, and specifically binds to the analyte analog. The combination thus forms an agent of the present invention.

In a yet further approach, the linking group is a protein, labelled with a suitable SE(R)RS active label and surface seeking group, and also conjugated to the targeted analyte. The protein-analyte conjugate portion may be that used as an immunogen to raise antibodies for use in the displacement assays (i.e. the analyte acts as a hapten).

Specificity of signature & agent structures

Where multiple analytes are being detected it will be necessary to use a SE(R)RS active label (or SE(R)RS modifying element) with a different chemical structure for each analyte, or class of analyte, that is being determined.

Thus if (for example) the azo group is used in multiple agents, these can be distinguished on the basis of the modifying effect on the azo signature of the groups conjugated to it (e.g. the surface seeking group, the analyte analog, or the linking group if present). If the same surface seeking groups are used in multiple agents, specificity must arise from the analyte analog and/or any linking groups present (see e.g. Example 2 and 3 below wherein dimethoxyaniline and drug residues are used in this way). The use of analyte-specific SERRS spectra will also, in preferred formats, permit the positive identification of the analyte.

In order to maximise the spectral differences between the analyte-analogs (e.g. drugs) with same label it is desirable that the drug be brought into proximity to the metal SER (R)S (e.g. silver) surface. This can be done in a number of ways.

Referring to FIG. 10(*a*), this shows a typical displacement agent for use in drug detection, incorporating a 'linker'

(which functions either to link different components and/or to modify the resonance frequency of the label—which in this case is the 'azo' group); a surface seeking group (here 'BT' or benzotriazole) and an analyte-analog (here 'drug'). In this case the metal SER(R)S surface is a silver surface. It will be appreciated that these structures types apply generally to other types of displacement agent of the present invention.

The TYPE A compound (as prepared in Examples 1 to 5, and FIGS. 1 to 5, and 6A and 6B below) shows a less preferred embodiment of the present invention. The 'drug' is spacially and sterically removed from the silver surface. The contribution of the drug structure to the SE(R)RS spectrum may be low.

TYPE B and TYPE C are more preferred labeled drug designs according to the present invention. In these formats the drug is brought closer to the silver surface by derivitising it to the surface seeking group, either directly or via the relatively small azo group. Steric hindrance does not prevent the drug entity approaching the silver surface and thereby contributing to the SE(R)RS spectrum. In these embodiments the 'linker' group serves to modify the resonance frequency of the dye.

Referring to FIG. 10($b$) this shows various of the agent-types discussed above. Molecules (i) and (iii) represent TYPE B compounds, whereas (ii) and (iv) represent TYPE C compounds. In (v) and (vi) the azo dye group is not present, as in the case wherein the drug itself is a chromophore, or perhaps where SERS is being used.

Molecular modeling of TYPE A and TYPE C labeled amphetamine compounds (not shown) shows that the amphetamine nucleus in the TYPE C compound is more proximal to the silver surface than that in the TYPE A compound.

3. SE(R)RS Surface-Seeking Activity

The agent must have a SE(R)RS surface-seeking group. This is a group which is readily adsorbed on to a suitable SE(R)RS surface in a selective manner, as discussed above. The adsorption may be of sufficient strength that the agent is effectively immobilised on to that surface.

The production of an agent incorporating these surface seeking dyes can be performed in the traditional manner by reacting the analyte or analyte/dye conjugate described above with the surface seeking molecule. For example, a labelled opiate required in an immunoassay method for the detection of the opiate class of drugs, can be obtained by using the opiate codeine as the starting material.

The interaction between the surface seeking group with the SE(R)RS-active surface will typically be by chemisorption of the complex onto the surface, or by chemical bonding of the complex with a coating on the surface (see comments below regarding surface coatings) either directly or through a linking group.

Surface seeking molecules will generally be either complexing or chelating in nature, or will comprise bridging ligands or polymer forming groups.

Naturally the choice of such a group will depend on the nature of the surface (e.g. its charge and the presence or absence of an oxide or other layer) and of any surface coatings or other species (such as citrate reducing agents) associated with it, and also on the nature of the SE(R)RS active label. For most useful surfaces, the functional group preferably comprises a Lewis base. Ideally, it is actively attracted to the surface in use. For gold surfaces phosphorus and sulphur containing groups may be particularly preferred.

Thus suitable groups by which the agent may be bound to the active surface include complexing groups such as nitrogen, oxygen, sulphur and phosphorous donors; chelating groups; bridging ligands and polymer forming ligands.

Example structures

These are shown in FIGS. 6A1–6A4. In all structures it will be understood that attachment positions and substituents, where specified, are by way of illustration.

Preferred surface seeking groups comprise heterocycles which contain at least two heteroatoms selected from nitrogen, sulphur and phosphorous.

The triazole group (Formula A1) is rich in nitrogen lone pairs and seems to have a particular affinity for SE(R)RS-active surfaces such as metal colloids. Thus, incorporation of this group in the agent is particularly preferred, since it can increase the proximity of the label to the surface, the surface enhancement effect and, ultimately, the detection sensitivity.

The agent preferably contains the benzotriazole group (Formula A2), particularly when the SE(R)RS-active surface is silver- or copper-based which has a high degree of conjugation (especially when deprotonated) and is thus particularly amenable to SE(R)RS detection which relies on label resonance.

Benzotriazole derivatives (such as the 5-amino analog shown in Formula A3) may be readily obtained and can be coupled with existing labels (such as azo dyes) to give appropriately modified labels. Naturally other analogs are also embraced by the present invention.

Thus in preferred forms, the SE(R)RS active dye and a surface seeking molecule will be combined into a single group which can be conjugated to the analyte (or analog thereof) to form the agents of the present invention. Examples of such groups include azobenzotriazoles, typically formed by combining azo substrates with benzotriazole derivatives. Examples of azobenzotriazoles include 9-(carboxyethyl)-3-hydroxy-6-oxo-6H-benzotriazole, and substituted benzoic and naphthoic acid azo derivatives coupled to benzotriazole.

An example agent incorporating a preferred surface seeking molecule which can be SE(R)RS active is the 5-azobenzotriazole shown in Formula A4. The compound comprises an azo chromophore which increases the wavelength of the absorbance maximum of the label. Naturally other azobenzotriazoles are also encompassed.

In all example structures in which it appears, $R_9$ represents the analyte portion of the agent, optionally with a linker, and optionally also with further surface seeking groups. Different $R_9$ groups can provide the agents with their molecularly specific SE(R)RS spectra and antibody affinity.

Suitably the antibody-binding displacement agents of the present invention labels are encompassed by the Formulae A5 and A6 wherein:

In all cases the analyte analog portion of the agent will constitute one or more of $R_1$–$R_6$ groups, preferably selected from groups $R_1$–$R_5$. The following preferences therefore refer to those groups from $R_1$–$R_6$ not being the analyte analog.

Thus the remaining $R_1$–$R_6$ can represent any appropriate groups (including hydrogen), preferably selected from those listed below the formulae.

W, X, Y and Z are defined below the formulae. A more preferred sub-set of such compounds is those in which $R_1$, $R_2$, $R_3$, $R_4$ and $R_6$ are independently selected from hydrogen, $C_1$–$C_6$ alkyl, $C_1$–$C_6$ alkoxy, 6-membered aromatic rings, halogen, —COOH, —$SO_3H$, —$PO_4$, —SH, —PO, —$NR_7$ and $R_8$; $R_5$ can be as $R_1$ or alternatively —$NH_2$ or functionalised —COOH such as —$(CH_2)_n$—COOH where n is an integer from 1 to 6; and $R_7$ and $R_8$ are independently selected from hydrogen, $C_1$–$C_6$ alkyl (linear or branched chain) and unsaturated cyclic alkyl rings.

Most preferred forms of such labels are those in which $R_1$ and $R_2$ are both hydrogen, $R_3$ and $R_4$ are independently selected from hydrogen and methoxy, $R_5$ is either —COOH or —amino and $R_6$ is hydrogen.

The agents prepared in Examples 1 to 3 (see FIGS. 6B and 6C), are examples of falling within these formulae.

Formula A7 provides an alternative to the benzotriazole-based agents.

Functional groups on the surface seeking portion of the agents may include charged polar groups (e.g., amine, carboxyl, phosphate, thiol, hydroxyl), attracted to the surface or surface coating (e.g., to free amine groups in a polyamine coating). Examples of these are shown in Formula A8, wherein $R_9$ is as discussed above, and $R_{10}$ is independently selected from the groups listed in the figure, with no more than 3 of the $R_{10}$ groups in the formula being H. Preferably the $R_{10}$ groups in the formula, other than those which are H, are all the same, as exemplified by Formula A9 and A10.

Further alternative surface seeking groups are shown by Formulae A11, A12 and A13.

Formulae A14 and A15 show benzene and triazene substituted benzotriazoles which have previously been used as UV inhibitors, but which chelate strongly with copper, and could be employed in the agents of the present invention. In those used in the art, $R_1$ usually hydrogen, $R_2$ is alkyl groups, and $R_3$ is alkyl or aryl ester.

Formulae A16 to A19 show a variety of benzene-substituted groups based on, respectively, benzothiadiazole, benzimidazole, 2-amino benzothiazole, 2-aminobenzimidazole.

Formulae A20 and A25 show yet further alternatives to benzotriazoles: these include pyrimidines, imidazoles, benzthiazoles and benzothiadiazoles.

Other suitable surface seeking groups for the agent include the calixerines and the mercapto benzotriazoles.

What these groups have in common is that they are soluble in solution but interact preferentially with the SE(R)RS surface, for instance by forming flexible polymeric structures on it, or by utilising flexible 'bolus' type structures i.e. which have a number of complexing groups flexibly arranged but tightly bound around a central core.

Thus the SE(R)RS active agents such as those described herein can give antibody-binding coloured products which incorporate a surface-seeking benzotriazole group and an azo chromophore. These can be detected at a concentration of at least $10^{-16}$ M(see EXAMPLE 4.)

Further aspects of the present invention

The agents described above per se form a further aspect of the present invention. In particular an agent which has the following characteristics:

(i) it is capable of specifically binding an antibody raised to any of the analytes discussed in the preferred embodiments of the invention above, (ii) it is SE(R)RS active as defined above, (iii) it is SE(R)RS surface-seeking, as defined above, Preferably the SE(R)RS activity arises from the azo group. Preferably the agent comprises a linking group. Preferably the analyte-analog portion of the agent, which permits specific binding to an antibody specific for the analyte, will make a detectable contribution to the SE(R)RS spectrum when the agent is detected on a SE(R)RS surface.

A further aspect of the invention is a method of producing an agent as described above.

The method preferably comprises the use of 3,5-dimethoxy aniline, which can serve to modify the SE(R)RS active label which may provide an agent-specific SE(R)RS signature via interaction with the antibody-binding portion of the agent. Naturally other compounds, including other substituted anilines or extended aromatic (optionally heterocyclic) compounds may be used (as described above), particularly those which have an amine group to assist derivatisation.

Preferably the agent produced by the process comprises the analyte which was used to raise the antibody (possibly used in hapten-protein conjugate form) but the process by which the agent is produced does not include that analyte as a starting material i.e. the analyte structure is itself formed by the conjugation of a SE(R)RS active or surface seeking molecule with other materials, for instance by an addition reaction to an analyte precursor. This approach, exemplified in Example 1 and FIG. 6C below, may increase the range of agents which can be used in the methods of the present invention. Preferably the agent is one which is specific for anti-amphetamine, or other drugs or therapeutics such as ephedrine and dopamines.

In a further aspect, the invention also includes an instrument suitable for use in the methods of the present invention, and use thereof in the detection and quantification, and more preferably identification, of analytes, particularly multiple analytes simultaneously.

A commercial SE(R)RS analyzer of use in carrying out the invention would be expected to consist of the following components: a laser light source (for instance housed in Raman spectrometer), the appropriate optics for carrying the light to the SE(R)RS active surface, an area for analysing displaced agent (e.g. glass capillary), optics for receiving the Raman signal, a detector for converting the Raman signal into a series of intensities at certain wavelengths and a data processor for interpreting the wavelength/intensity data and providing an analytical output.

The light source, optics, detector and processor have already been referred to above.

Figure 7:
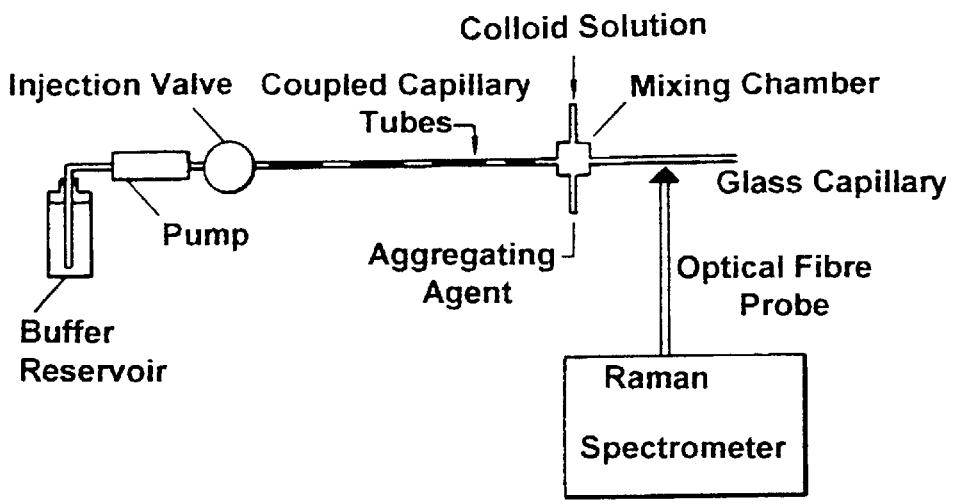

In preferred embodiments forms there is provided a 'continuous flow' displacement SE(R)RS immunoassay sensor system capable of screening for more than one analyte in a mixture. An example design is shown in FIG. 7 below. As described above, this will comprise antibodies, specific for each analyte being assayed, to be immobilized on the inner surfaces of separate lengths of capillary tubes (glass, polypropylene etc.,). Each tube is then saturated with its corresponding SE(R)RS agent—the agents are not identical and therefore produce different spectra which provides discrimination between the analytes and hence no need for any physical separation of the analytes. These tubes after washing are joined together with another length capillary tube after the final antibody coated tube.

The steps in the process are described in FIG. 8. In this figure the agents are shown as consisting of directly labelled analytes. However any agents of the present invention could be used.

Since a different label is used for each analyte and they give different spectra, computer searching and matching routines can be use to confirm which analytes are present in the mixture. This approach overcomes any need to physically separate the analytes in a mixture. See EXAMPLE 5.

Preferably the apparatus is portable i.e. is designed such that it can be readily operated in different locations; for instance it may incorporate an internal power supply and weigh less than 15–20 lb.

In an alternative embodiment, there is provided a 'static' immunosensor.

In this design the antibody specific to each analyte or class of analyte being targeted are immobilised on separate batches of magnetic beads. After washing, a quantity of each of beads having the different antibodies immobilised thereon are mixed together in a tube. The sample (if a liquid) is then introduced into the tube if any targeted analytes are present these will displace the corresponding labelled analytes. The magnetized beads are then drawn to the bottom of the tube. After addition of the silver colloid and aggregating reagent and focussing the fibre optic probe on the solution in the tube a SE(R)RS spectrum of the displaced labelled analytes is recorded. if the sample is breath or air the adsorption/desorption procedure described above can be used.

An alternative method to putting the different antibodies immobilized on magnetic beads into one tube, is to place an aliquot of each into separate wells of a micro-titre plate. The same procedure is then followed as above to displace the labelled analyte prior to recording the SE(R)RS spectrum of the contents of each well.

Both of these techniques can be performed manually or automatically. If using a micro-titre plate the SE(R)RS spectra of each well can be recorded automatically by placing the plate on an x-y motorized stage with the optical fibre probe set in a fixed position or alternatively, keeping the plate in a fixed position and scanning the optical fibre probe over the wells in the micro-titre plate.

In a further aspect of the present invention there are disclosed kits or other components for use in carrying out the method of the present invention. These may include any one or more of the following:

1) One or more capillary tubes containing immobilised antibodies and agents (preferably in the form of an immune complex) of the present invention. Preferably more than one tube, each containing a different antibody (and agent) is provided. More preferably the tubes are adapted to be combined into a single channel, for instance by having being adapted to slide fit into each other. Optionally joining-means are provided separately (e.g. sleeves to help join the tubes).

2) Magnetic beads having immobilised antibodies and agents (preferably in the form of an immune complex) of the present invention.

3) One or more standard solutions for calibrating the apparatus and components described above, for instance containing the agents of the present invention in known concentration.

4) two or more agents, each having the same surface seeking group, azo dye, and linker, but differing in the nature of the analyte which makes up the other portion of the agent.

The various aspects of the invention will now be further described with reference to the following non-limiting Examples and Figures. Further embodiments falling within the scope of the present invention will occur to those skilled in the art in the light of these.

FIGURES

FIG. 1—SE(R)RS spectrum of the labelled codeine derivative at a concentration of $10^{-7}$M. Wavelength 514.5 nm.

FIG. 2—SE(R)RS spectrum of the labelled amphetamine at a concentration of $10^{-7}$M. Wavelength 514.5 nm.

FIG. 3—SE(R)RS spectrum of the labelled methylamphetamine at a concentration of $10^{-7}$M. Wavelength 514.5 nm.

FIG. 4—SE(R)RS spectrum of the labelled amphetamine at a concentration of $10^{-16}$M. Wavelength 514.5 nm and high laser power output.

Figure 5:
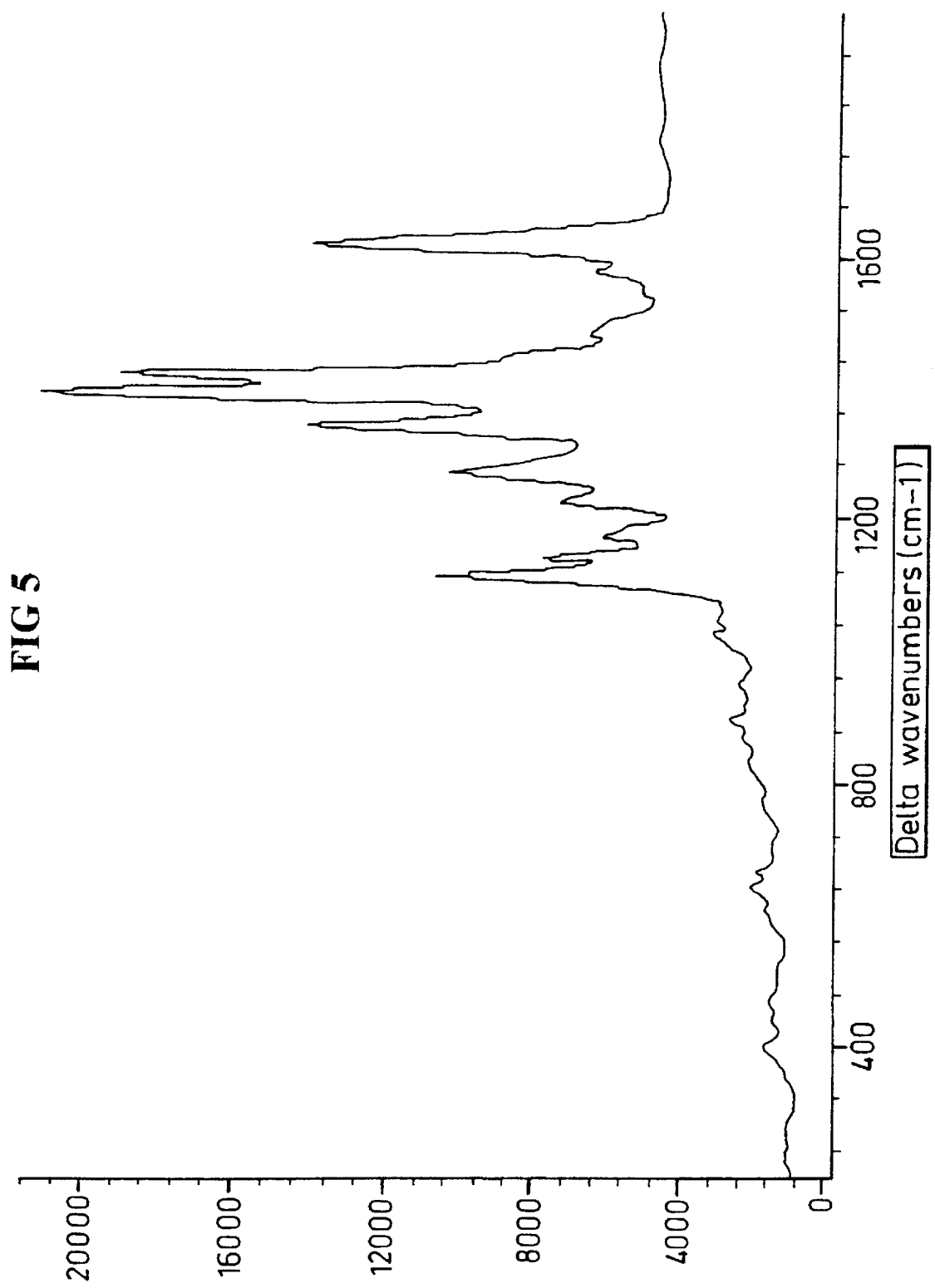

FIG. 5—SE(R)RS spectrum of a mixture containing the labelled amphetamine, methylamphetamine and codeine. Concentration of each label is $10^{-8}$M and laser wavelength of 514.5 nm.

FIGS. 6A1–6A4-Formulae A1–A25: various surface seeking groups and agents of the present invention.

FIG. 6B—synthesis of codeine (an opiate) derivative using the drug as a starting material.

FIG. 6C—synthesis of amphetamine and methyamphetamine derivatives using dimethoxyaniline, wherein the drug is not a starting material.

FIG. 7—apparatus for continuous flow immunoassay

Figure 8A:
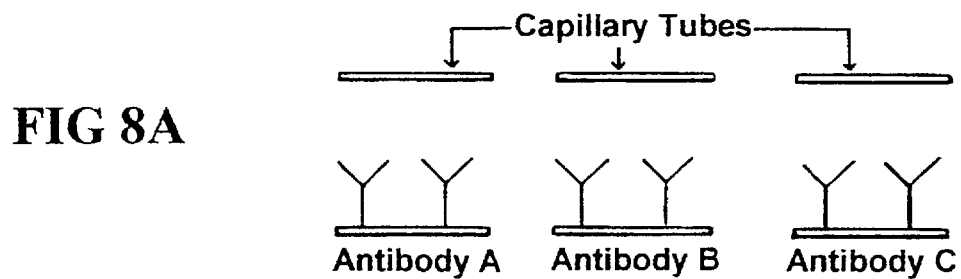
Figure 8B:
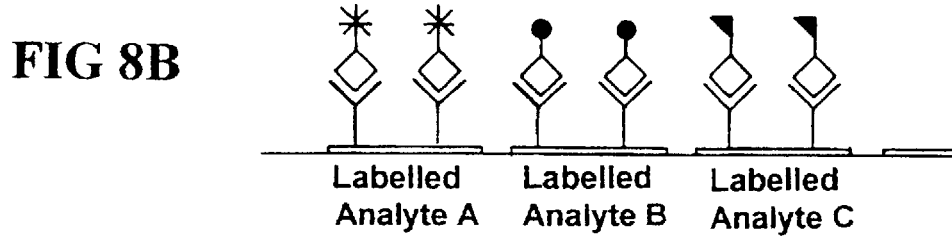
Figure 8C:
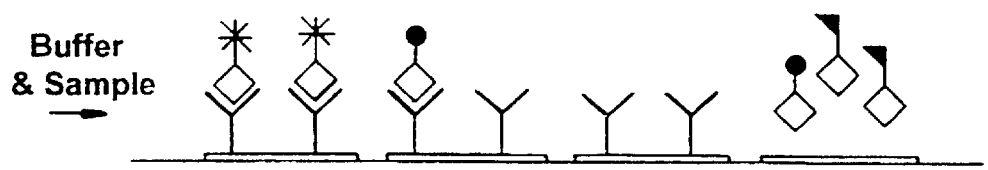

FIGS. 8A–8C—schematic diagram showing displacement of multiple agents from respective capillary tubes simultaneously by a sample. FIG. 8A shows the capillary tubes with immobilised antibodies. In 8B, agents have been added and the tubes joined. In 8C, certain of the agents are selectively displaced by a sample containing corresponding analytes.

Figure 9A:
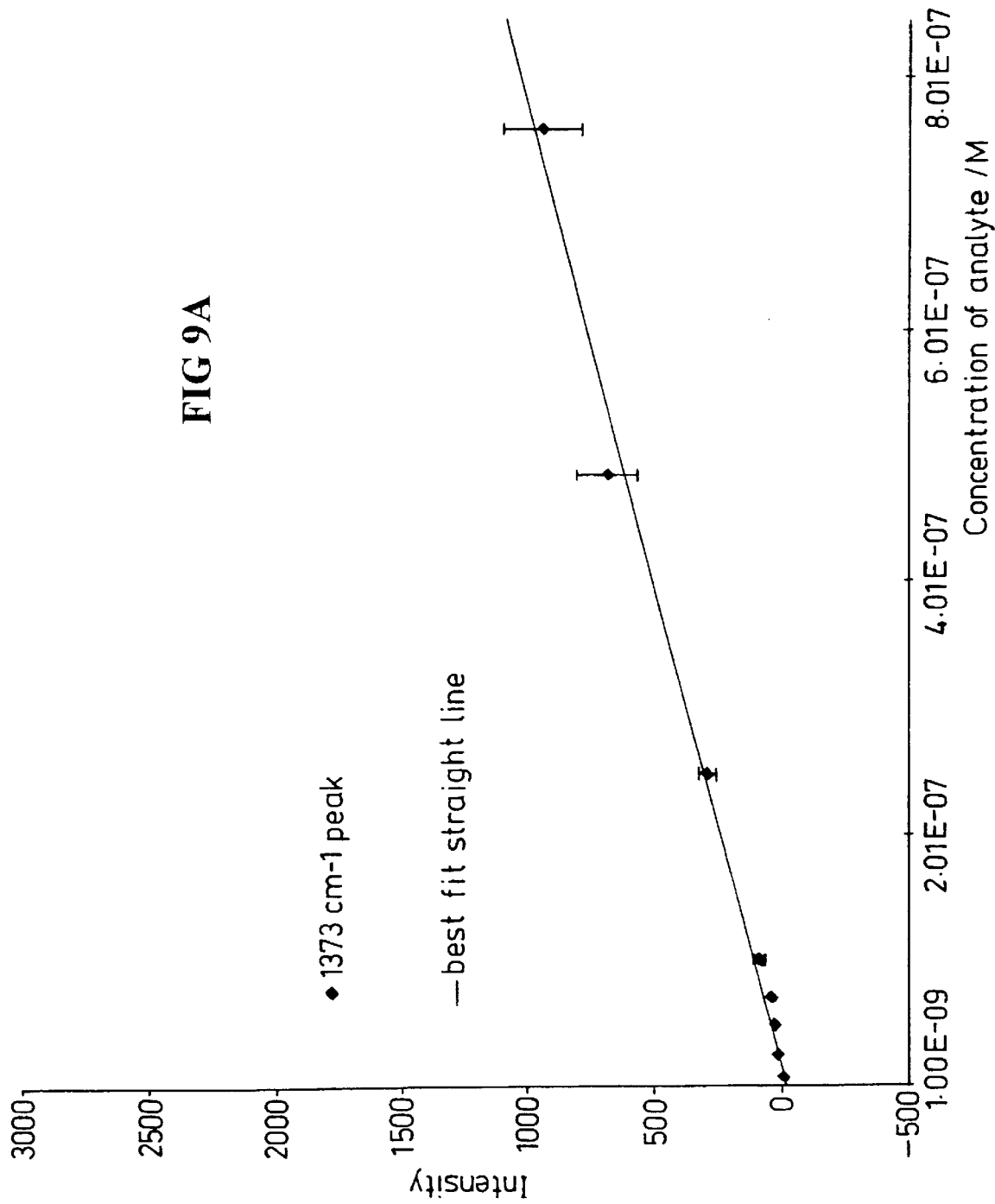

FIGS. 9A and 9B—SERRS signal/concentration response profiles. FIG. 9A shows that for 3,5-dimethoxyazobenzotriazole (a SERRS active, surface seeking group) while FIG. 9B shows the profile for the same group after it has been conjugated to an amphetamine, as described in Example 7.

Figure 10A:
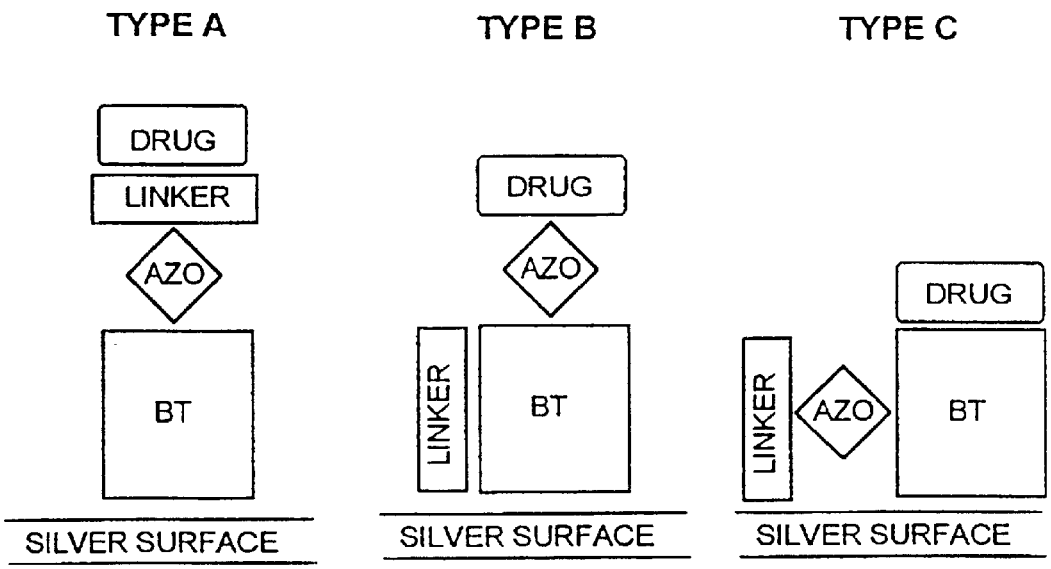
Figure 10B:
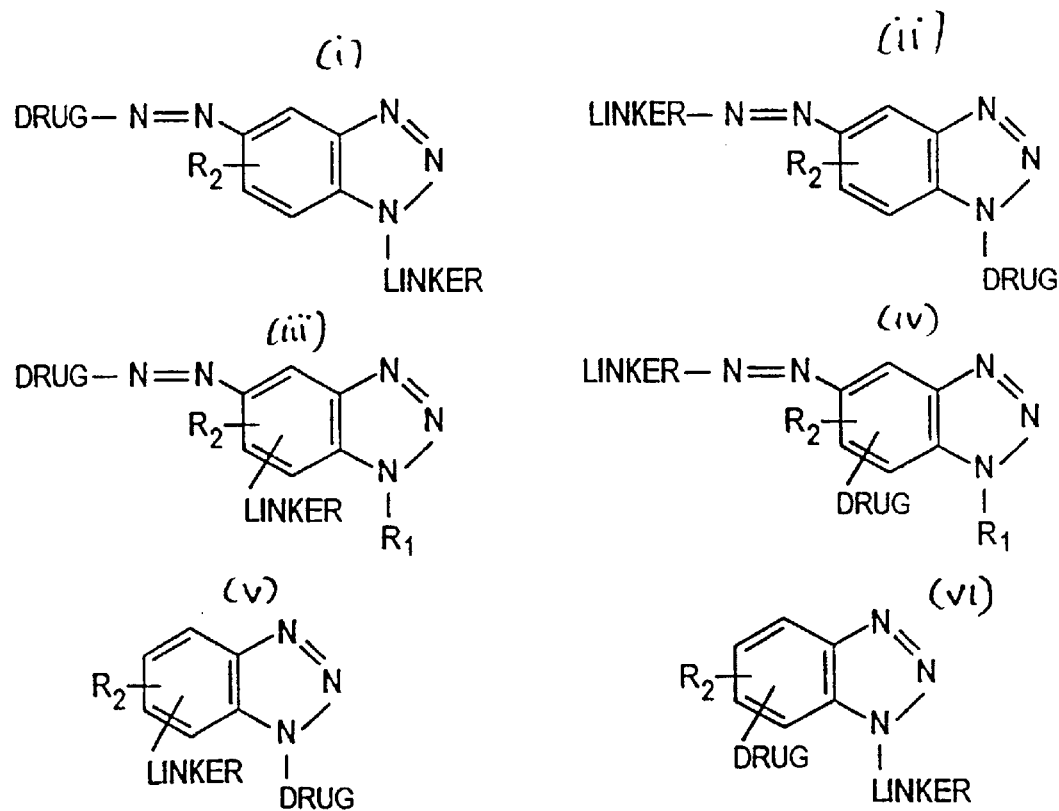

FIGS. 10(a) and 10(b) show typical displacement agents for use in drug detection, incorporating a 'linker'; a surface seeking group and an analyte-analog. In the TYPE A compound the 'drug' is spacially and sterically removed from the silver surface. The contribution of the drug structure to the SE(R)RS spectrum may be low. In TYPE B and TYPE C compounds the drug is brought closer to the silver surface by derivitising it to the surface seeking group, either directly or via the relatively small azo group.

Figure 11:
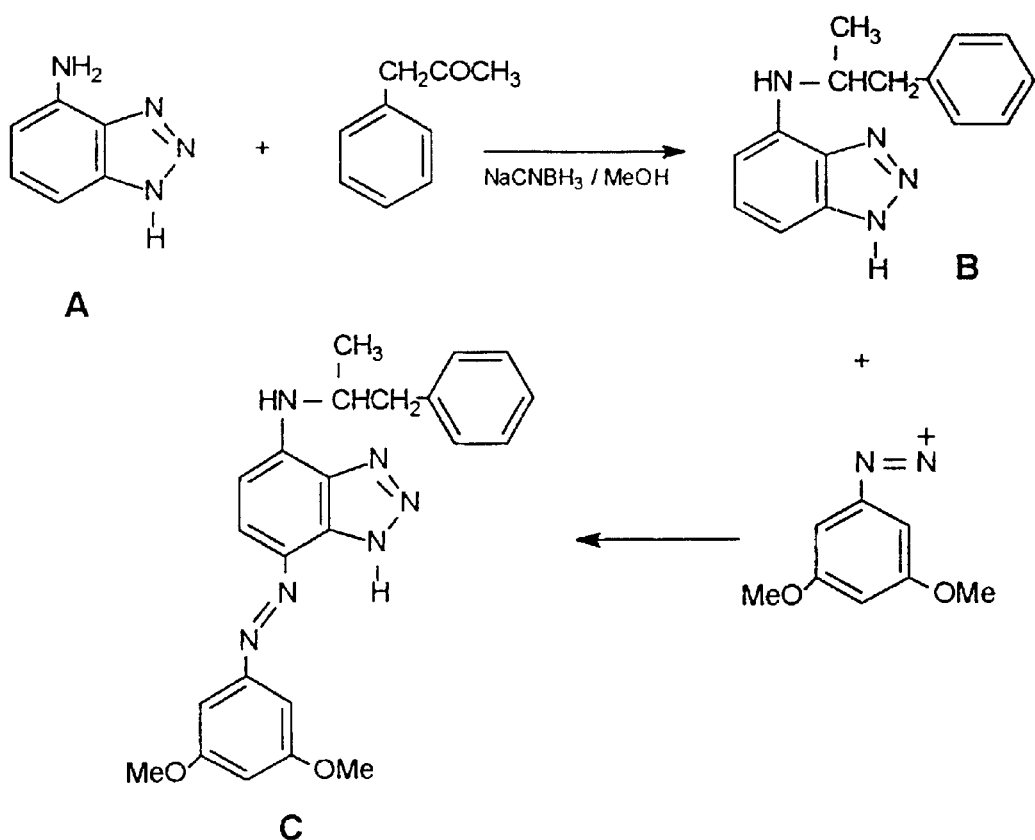

FIG. 11 shows the synthetic route used to prepare 'TYPE C' 3,5-dimethoxybenzene-4-(7-azobenzotriazole)-N-amphetamine, as in described in Example 8.

EXAMPLES

Example 1

Preparation of Aminonaphthalene-4-(5'-azobenzotriazole)-N-codiene.

This is a two stage synthesis and the product from the first stage was isolated and characterized prior to proceeding to the second stage.

Stage 1—Preparation of naphthalene-1-N-amino-codiene

Codiene (1 g: 3.35 mol) was added to a solution of 1-amino-naphthalene (0.47 g: 3.35 mol) in glacial acetic acid (1 ml) and methanol (50 ml). Sodium cyanoborohydride (1.5 g: 1.38 mol) was added and the mixture stirred at room temperature for 3 days, by which time TLC (silica plate and dichloromethane) showed complete reaction. Hydrochloric acid (20 ml: 2M) was added and the methanol was removed in vacuo to leave the aqueous layer. The mixture was extracted with dichloromethane (4×150 ml) and the combined organic solution was dried over magnesium sulphate. After filtering the organic solution was evaporated in vacuo to leave an oil.

This oil was purified on a silica column with dichloromethane, and the fractions collected were combined and the solvent was removed, in vacuo to give colourless oil.

This oil was crystallized from ethanol to give white crystals, (1.2 g: 85% yield).

Melting Point: 150–151° C.

$^1$H NMR, 400 MHz in DMSO-$d_6$; 7.75–7.82 (2H, dd, Ar-H); 7.44 (2H, dt, Ar-H); 7.41 (7H, dd, Ar-H); 7.38 (1H, d, Ar.-H); 6.78 (1H, d, Ar-H); 6.72 (2H, d, Ar-H); 6.65 (1H, d, Ar-H); 3.72 (3H7 o-methoxy); 3.18 (1H, br,m, H-9); 2.92 (2H, d, H-10); 2.40 (3H, N-Me); 1.69 (1H, M, C-H, codeine); 1.56–1.70 (3H, m, CH-codeine); 1.16–1.14 (2H, m, CH$_2$-codeine); 1.25–1.05 (1H, m, CH-codeine).

Mass Spectrometry—FAB: m/z MH$^+$; 426.

Microanalysis: Determined for $C_{28}$ $H_{29}$ $N_2$ $O_2$. 1.5H$_2$O

Calculated: C, 74.40; H, 7.25; N, 6.77. Found: C, 74.11; H, 7.11; N, 6.61.

Stage 2—Preparation of aminonaphthalene-4-(5'-azobenzotriazole)-N-codeine.

Sodium nitrite (300 mg: 3.25 mol) in water (3 ml) was added dropwise at 0° C. over 10 minutes to a solution of 5-aminobenzotriazole (350 mg 2.61 mol) in hydrochloric acid (4 ml; 50% v/v). The mixture was stirred at room temperature, then added dropwise to a stirred solution of naphthalene-1-N-amino codeine (0.5 g; 1.17 mol) in pH 6 sodium acetate buffer (4 ml: 1M). After a while the reaction mixture thickened and to facilitate stirring acetone was added. Stirring was continued for 16 hours at room temperature. After filtering the crude product was purified on a silica column with dichloromethane/methanol (5:1) as the eluent. The solvent was removed in vacuo from the collected fractions to leave a dark purple/red oil. By trituration of the oil with ethanol and ether a dark purple product was formed which was recrystallized from ethanol/acetone to give 130 mg (yield 20%) of the product.

100 mg of this material was dissolved in absolute alcohol (2 ml) and a solution of an excess of oxalic acid in ether was added and allowed to stand at room temperature for 1 hour. A precipitate was formed on the addition of ether and removed by filtration. This was crystallized from ethanol/acetone to give 65 mg of the purple oxalate salt of the product.

Melting Point: 165–167° C.

Infrared: Liquid film in Nujol; 3172–3376 cm$^{-1}$ (N—H str); 1590 cm$^{-1}$ (C=C); 867–719 cm$^{-1}$ (substituted benzene).

$^1$H NMR 400 MHz in DMSO-$d_6$: 7.78 (1H, d, Ar-H); 7.67 (1H, d, Ar-H); 7.42–7.44 (2H, m, Ar-H), 7.39–7.42 (2H, t, Ar-H); 7.38 (1H, d, Ar-H); 6.80 (1H, d, Ar-H); 6.71 (1H, d, Ar-H); 6.61 (1H, d, Ar-H); 4.92 (1H, d,j=7.06 Hz, H-8 codeine); 4.78 (1H, d,j=14.6 Hz, H-7 codeine); 3.84 (1H, m, H-6 codeine); 3.73 (3H, s, OMe); 3.38 (1H, m, H-9 codeine); 3.01–3.11 (2H, m, CH$_2$-codeine); 2.54–2.68 (2H, m, CH$_2$-codeine); 2.45 (3H, s, NMe); 2.11 (1H, dt, CHcodiene); 1.71–0.87 (3H, m, CH-codeine).

Mass Spectrometry: FAB m/z MH$^+$ 573

Microanalysis: Calculated for $C_{34}H_{33}N_7O_2$. 3$C_2H_2O_4$.

Calculated: C, 53.86; H, 4.84; N, 13.20. Found: C, 53.85; H, 4.22; N, 13.77.

| | | |
|---|---|---|
| UV: | $\lambda_{max}$ | 469.4 nm in methanol at 10$^{-5}$ M. |
| | | 564.0 nm in methanol + 1 M hydrochloric acid |
| | | 471.4 nm in methanol + 1 M sodium hydroxide |

SE(R)RS: A SE(R)RS spectrum of the compound is shown in FIG. 1.

Concentration 10$^{-7}$M and laser wavelength of 514.5 nm.

Example 2

Preparation of 3,5-dimethoxybenzene-4-(5'-azobenzotriazole)-N-amphetamine

This is a two stage synthesis and the product from the first stage was isolated and characterized prior to proceeding to the second stage.

Stage 1—Preparation of 3,5-dimethoxybenzene-N-amphetamine.

Phenylacetone (500 mg: 3.7 mol) was added to a solution of 3,5-dimethoxyaniline (1,4 g: 0.074 mol) in glacial acetic acid (1 ml) and methanol (50 ml). Sodium cyanoborohydride (0.99: 0.142 mmol) was added and the mixture stirred at room temperature for 3 days, by which time TLC (silica plate and dichloromethane) showed complete reaction. Hydrochloric acid (20 ml: 2M) was added and the methanol was removed in vacuo to leave the aqueous layer. The mixture was extracted with dichloromethane (4×150 ml) and the combined organic solution was dried over magnesium sulphate. After filtering the organic solution was evaporated in vacuo to leave an oil.

This oil was purified on a silica column with dichloromethane/hexane (2:1 v/v) and the fractions collected were combined and the solvent was removed in vacuo to give a colourless oil (1 g; Yield 99%).

A small amount of this oil (10 mg) was dissolved in ether and anhydrous oxalic acid (1.5 eq) in ether (4 ml) was added. A precipitate was formed by the addition of an excess of dry and this was filtered off, washed with ether and dried to give a white solid (80 mg).

Melting Point: 157–158° C.

Infrared: Liquid film in Nujol; 3394 cm$^{-1}$ (N—H str); 3021 cm$^{-1}$ (CH str,unsaturated); 2838 and 2929 cm$^{-1}$ (CH, str) 1612 cm$^{-1}$ (C=C); 1201 cm$^{-1}$ (OMe); 689–742 cm$^{-1}$ (substituted benzene).

$^1$H NMR 400 MHz in CDCl$_3$: 7.23–7.38 (5H, m, Ph-amphetamine); 5.94 (1H, s, (Ar-H); 5.80–5.9Q (2H, t, Ar-H), 3.81 (7H, m 2×OMe+CH-amphetamine); 2.95–3.05 (1H, m, CH$_2$-amphetamine); 2.77–2.79 (1H, ms, CH$_2$-amphetamine); 1.18–1.22 (3H, d, CH$_3$-amphetamine).

Mass Spectrometry: EI$^+$ m/z; 271.

Microanalysis: Calculated for $C_{17}H_{21}NO_2$. 0.8 $C_2H_2O_4$.

Calculated: C, 65.11; H, 6.39; N, 4.20. Found: C, 65.07; H, 6.64; N, 4.08.

Stage 2—Preparation of 3,5-Dimethoxybenzene-4-(5'-azobenzotriazole)-N-amphetamine Sodium nitrite (175 mg: 2.05 mol) in water (2 ml) was added dropwise at 0° C. over 10 minutes to a solution of 5-aminobenzotriazole (225 mg: 2.61 mol) in hydrochloric acid (4 ml; 50% v/v). The mixture was stirred at room temperature, then added dropwise to a stirred solution of 3,5-dimethoxybenzene-N amphetamine (500 mg: 3.73 mol) in pH & sodium acetate buffer (4 ml: 1M). After a while the reaction mixture thickened and to facilitate stirring acetone was added. Stirring was continued for 16 hours at room temperature. After filtering the crude product was purified on a silica column with dichloromethane/methanol (5:1) as the eluent. The solvent was removed in vacuo from the collected fractions to leave a dark red oil. By trituration of the oil with ethanol and ether a red product was formed which was recrystallized from ethanol/acetone to give 300 mg (yield 50%) of the product.

Melting Point: 169–171° C.

Mass Spectrometry: El$^+$ m/z; 416

Infrared: KBr Disc, 3440 cm$^{-1}$, (OH-water), 3227 cm$^{-1}$ (N—H str), 1635 cm$^{-1}$ (N=N), 1569 cm$^{-1}$ (C=C), 1259 cm$^{-1}$ (Ome), 710–821 cm$^{-1}$ (substituted benzene)

$^1$H NMR 400 MHz in DMSO-d$_6$: 12.63 (1H, brs, N—H); 10.25 (1H, brs, NH), 7.81 (2H, d, Ar-H-benzotriazole); 7.26–7.32 (5H, m, Ph-amphetamine); 7.18–7.20 (1H, m, Ph-amphetamine); 6.03 (1H, brs, Ar-H); 5.75 (1H, brs, Ar-H); 4.43 (1H, brt, CH-amphetamine): 4.04 (6H, 2×methoxy). 2.86–2.92 (2H, m, CH$_2$-amphetamine); 1.31 (3H, d, CH$_3$-amphetamine).

Microanalysis: Calculated for $C_{27}H_{23}N_6O_2$. 4 $C_2H_2O_4$. 0.5 H$_2$O

Calculated: C, 53.12; H, 4.63; N, 11.12. Found: C, 53.47; H, 4.40; N, 10.90.

UV: In methanol at a concentration of $10^{-10}$M $\lambda_{max}$=462.4 nm.

SE(R)RS: A SE(R)RS spectrum of the compound is shown in FIG. 2. Concentration $10^{-7}$M and laser wavelength of 514.5 nm.

Example 3

Preparation of 3,5-Dimethoxybenzene -4-(5'-azobenzotriazole)-N-methyl-amphetamine.

This is a two stage synthesis and the product from the first stage was isolated and characterized prior to proceeding to the second stage.

Stage 1—The preparation of 3,5-dimethoxybenzene-N-methylamphetemine.

Formaldehyde (40%; 1.5 ml) was added to a solution of 3,5-dimethoxy-N-methylamphetamine (1,4 g: 0.074 mol) in glacial acetic acid (0.3 ml) and methanol (30 ml). Sodium cyanoborohydride (0.5 g: 0.08 mol) was added and the mixture stirred at room temperature for 3 days, by which time TLC (silica plate and dichloromethane/hexane, 2:1) showed complete reaction. Hydrochloric acid (20 ml: 2M) was added and the methanol was removed, in vacuo to leave the aqueous layer. The mixture was extracted with dichloromethane (4×150 ml) and the combined organic solution was dried over magnesium sulphate. After filtering the organic solution was evaporated in vacuo to leave an oil.

This oil was purified on a silica column with dichloromethane/hexane (2: 1 v/v) and the fractions collected were combined and the solvent was removed in vacuo to give a colourless oil (0.45 g; yield 78%).

A small amount of this oil (100 mg) was dissolved in ether and anhydrous oxalic acid (1.5 eq) in ether (4 ml) was added. A precipitate was formed by the addition of an excess of dry and this was filtered off, washed with ether and dried to give a white solid (70 mg).

Melting Point: 102–104° C.

Infrared: Liquid film in Nujol; 3394 cm$^{-1}$ (N—H str); 3021 cm$^-$(CH str, unsaturated, 2838 and 2929 cm$^{-1}$ (CH str); 1612 cm–1 (C=C); 1201 cm$^{-1}$ (O-methoxy) 689–742 cm$^{-1}$ (substituted benzene).

$^1$H NMR 400 MHz in CDCl$_3$: 7.27–7.78 (5H, m, Ph-methylamphetamine); 6.1 (1H, s, Ar-H); 5.80–590 (2H, s, Ar-H); 3.77–4.4 (1H, m, CH-methylamphetamine); 3.49 (6H, s, 2×methoxy); 2.70–3.01 (1H, m, CH$_2$-methyiamphetamine); 2.22–2.48 (1H, m, CH$_2$-methylamphetamine); 2.65 (2H, d, N-CH$_3$-methylamphetamine), 1.18–1.22 (3H, dd, CH$_3$-methylamphetamine).

Mass Spectrometry: El$^+$ m/z; 285

Stage 2—Preparation of 3,5-dimethoxybenzene-4-(5'-azobenzotriazole)-N-methylamphetamine.

Sodium nitrite (120 mg:1.41 mol) in water was added dropwise at 0° C. over 10 minutes to a solution of 5-aminobenzotriazole (225 mg: 0.83 mmoi) in hydrochloric acid (4 ml; 50% V/V). The mixture was stirred at room temperature, then added dropwise to a stirred solution of 3,5-dimethoxybenzene-N-methyl amphetamine (230 mg: 0.8 mol) in pH 6 sodium acetate buffer (4 ml: 1M). After a while the reaction mixture thickened and to facilitate stirring acetone was added. Stirring was continued far 16 hours at room temperature. After filtering the crude product was purified on a silica column with dichloromethane/methanol (5:1) as the eluent. The solvent was removed in vacuo from the collected fractions to leave a dark red oil. By trituration of the oil with ethanol and ether a red product was formed which was recrystallized from ethanol/acetone to give 70 mg (yield 21%) of the product.

UV: $\lambda_{max}$ at 470.4 nm in methanol at a concentration of $10^{-5}$M

SE(R)RS: A SE(R)RS spectrum of the compound is shown in FIG. 3. Concentration $10^{-7}$ and laser wavelength of 514.5 nm.

Example 4

Sensitivity Achieved with SE(R)RS

A stock solution of the labelled amphetamine (3,5-dimethoxybenzene-4-(5'azobenzotraizole)-N-amphetamine) in water was prepared. Serial dilutions of this solution were prepared down to a concentration of $10^{-15}$M. For each dilution an aliquot (100 μl) was mixed with water (500 μl), silver colloid (500 μl) and aqueous poly(L-lysine) solution (0.01%; 100 μl). The spectrum obtained for the lowest concentration of $10^{-15}$ M is shown in FIG. 4. A 514 nm laser wavelength on a high power output setting was used to irradiate the sample. Note that in preparing the sample the addition of the other reagents diluted the sample by a factor of 10, hence the amphetamine label was analysed at a final concentration of $10^{-16}$M.

At this concentration strong SE(R)RS signals are still obtained. In comparison with a concentration of $10^{-7}$M (FIG. 2) no changes can be detected in the position of these signals, thus indicating that it is possible to identify the labelled amphetamine at a concentration of $10^{-16}$M confirming the outstanding sensitivity that can be achieved, whilst still retaining the qualitative information.

Example 5

SE(R)RS Analysis of Labelled Analytes in a Mixture

It can be observed that there are distinct features in the SE(R)RS spectra of the labelled amphetamine, methylamphetamine and codeine compounds (FIGS. 1–3). The differences between the spectra of the amphetamine and methylamphetamine also highlight further the selectivity of SE(R)RS spectroscopy because both compounds have been tagged with the same label. Therefore, discrimination is due to their different molecular structures and this is very impressive since the difference between these molecules is only one methyl group. It is due to this selectivity of SE(R)RS that several analytes which are tagged with their own SE(R)RS active label, can be detected and identified in a mixture. To confirm this, a mixture containing the labelled products of amphetamine methylamphetamine and codiene was prepared and analysed as follows.

An aliquot of each labelled compound ($10^{-8}$M in water; 150 μl) was mixed with water (250 μl), silver colloid (250 μl) and an aqueous solution of poly(l-lysine) (0.01%; 80 μl). This sample was irradiated with a laser at 514.5 nm (low output power) and the spectrum obtained is shown in FIG. 5. From the spectra of the individual compounds it is possible to identify visually the major signals and hence confirm that these compounds are present in the mixture.

Example 6

Apparatus for performing the present invention

This is shown in FIG. 7. In use samples can be introduced as solutions via an injection valve. In the case of air or breath samples these can be collected on small particles of an adsorbent e.g., Tenax retained in a tube. The adsorbed analytes can then be desorbed with a solvent to provide a solution—an aliquot can then be injected onto the system. Alternatively an inert gas can be passed through the Tenax tube which is heated and the desorbed analytes are collected in a solvent and sampled as for a liquid solution. These sampling procedures can be performed manually or can be automated.

To prepare the capillary tubes of the apparatus, prior to linking together, an antibody specific for a compound or class of compounds is immobilized on the inner surface of each capillary tube which is then saturated with the SE(R)RS labelled target compound designed to form a complex with the antibody. Different tubes are prepared in a similar manner for each of the targeted compounds. A buffer is pumped through the capillary tubes at a constant flow rate and an aliquot of a sample solution is injected via a valve into the following stream. Any target analytes in the sample displace their corresponding SE(R)RS labelled compounds from the antibodies. On leaving the final length of the capillary, the eluate containing the mixture of SE(R)RS labelled analytes enters an in-line micro-volume mixing chamber into which silver colloid and an aggregating agent are pumped before continuing to through a capillary which is irradiated (optionally via an optical fibre) with the laser beam of the Raman spectrometer. Raman spectra are captured via a probe and recorded at time intervals, and from these the target compounds if present in the sample are detected and identified. The strength of the signals can be used to quantitate the amount of targeted analyte present.

Example 7

SERRS signal/concentration response profiles. FIG. 9A shows that for 3,5-dimethoxyazobenzotriazole (a SERRS active, surface seeking group). FIG. 9B shows the profile for 3,5-dimethoxyazobenzene-4-(5'azobenzotriazole)-N-amphetamine. The samples and analytical conditions were as per Example 4. Both graphs illustrate the linearity of the SERRS signal over a wide range of concentrations of these azobenzotriazoles. Note that $10^{-4}$ M in FIG. 9B represents levels of surface density greater than monolayer coverage. At that level, linearity may no longer be achieved.

Example 8

Labeled compounds of amphetamine and diethylpropion were prepared based upon the TYPE C structural arrangement—see FIG. 10(a). The same linker molecule, 3,5-dimethoxyaniline was used for both drug labels. The method described in detail below (and shown in FIG. 11) for the preparation of the amphetamine labeled compound was also used for the synthesis of the labeled diethylpropion.

Synthesis of 3,5-Dimethoxybenzene-4-(7-azobenzotriazole)-N-amphetamine

STAGE 1—Preparation of 4-N-amphetaminebenzotriazole (B)

Benzylmethylketone (0.8 g: 5.97 mmol) was added to a solution of 4-aminobenzotriazole (0.8 g; 5.97 mmol) in methanol (30 ml) and glacial acetic acid (0.3 ml). Sodium cyanoborohydride (2 g; 31.74 mmol) was added and the mixture was stirred at room temperature for 3 days, by which time TLC (silica/diethyl ether) showed complete reaction. Dilute hydrochloric acid was added and the methanol was removed in vacuo to leave the aqueous phase. This mixture was extracted with ethyl acetate (4×150 ml) and the combined organic layers were dried over magnesium sulphate and removed in vacuo to leave an oil. This was purified on a silica column using diethyl ether as the eluting solvent. The eluate was evaporated give the product as a brown oil.

STAGE 2—Preparation of 3,5-Dimethoxybenzene-4-(7-azobenzotriazole)-N-amphetamine (C)

Sodium nitrite (200 mg; 3.07 mmol) in water (2 ml) was added dropwise at 0° C. over 10 minutes to a solution of 3,5-dimethoxyaniline (430 mg; 2.77 mmol) in hydrochloric acid (3 ml; 50%). The mixture was stirred at room temperature for 15 minutes and then added dropwise to a stirred solution of B (700 mg; 2.77 mmol) in sodium acetate buffer (1M; pH 6; 4 ml). After a period the mixture became thick and acetone was added and the mixture was stirred for 16 hours at room temperature. The mixture was filtered and the crude solid material was purified on a silica column using an eluent of dichloromethane/methanol (5:1). The fractions collected were combined and the solvent removed in vacuo to leave a dark red oil. A brown yellow product was formed by trituration from benzene and hexane. Recrystallization from benzene gave yellow brown crystals (300 mg; 21% yield) of the desired product C.

Melting Point–140–141° C.

Mass Spectrometry-m/z of 416=M$^+$. Accurate Mass= 416.18457 $^1$H NMR-(400 MHz; solvent DMSO-$d_6$) 15.6 (IH,s;NH); 7.90 (1H,d;ArH); 7.74 (1H,d;ArH); 7.5–7.36 (5H,m; Ph-amphetamine); 7.15 (1H,t; ArH); 6.59 (1H,d; ArH); 6.53 (1H,d; ArH); 4.50 (1H,br; NH); 3.83 (6H,s; 2MeO); 3.48 (1H,brs; C$\underline{H}$(CH$_3$)); 3.08 (1H,m; C$\underline{H}_2$-amphetamine); 2.84 (1H,m; C$\underline{H}_2$-amphetamine); 1.28 (3H,dd; C$\underline{H}_3$-amphetamine).

Microanalysis

Found: C, 66.84; H, 4.80; N, 20.16. Calculated: C, 66.34; H, 4.88; N, 19.95.

MOLECULAR MODELLING

Molecular modeling studies of TYPE A and TYPE C labeled amphetamine compounds with the same linker, 3,5-dimethoxyaniline, and the same silver surface seeking part (benzotriazole) were preformed. These structures confirmed that in the TYPE A structure the amphetamine is a considerable distance from the benzotriazole group and furthermore, there is steric hindrance by the azo and linker groups. In the TYPE C structure the amphetamine is much closer to the benzotriazole group and is not sterically hindered. Hence the amphetamine can experience surface enhancement which is manifested as SERRS spectra in which signals.can be attributed to the drug.

What is claimed is:

1. A method for detecting the presence or amount of a target analyte in a sample comprising the steps of:

(a) exposing the sample to a complex comprising an immobilized antibody capable of specifically binding the analyte, said antibody being specifically bound to a displacement agent, wherein said agent comprises:
   (i) an analyte analog portion, capable of specifically binding the antibody,
   (ii) a label, which has surface enhanced Raman scattering (SERS) activity, or surface enhanced resonance Raman scattering (SERRS) activity,
   (iii) a SERRS or SERS surface-seeking group,
whereby the analyte if present in the sample causes the displacement of the agent from the antibody;
(b) exposing the agent displaced from the antibody by the analyte to a SERRS or SERS surface such that said displaced agent becomes adsorbed on said surface; and
(c) detecting displaced agent associated with said surface using SERRS or SERS.

2. A method as claimed in claim 1 wherein the method is used to identify the analyte in the sample.

3. A method as claimed in claim 1 wherein more than one target analyte is detected from the sample simultaneously.

4. A method as claimed in claim 3 wherein multiple antibodies are used, each of said multiple antibodies is specific for a target analyte or class of analytes, and wherein each of said multiple antibodies is respectively bound to a corresponding agent having a distinctive SERRS or SERS spectrum .

5. A method as claimed in claim 4 wherein the SERRS or SERS spectrum of the agent is dependent on inherent properties of the analyte analog in said agent.

6. A method as claimed in claim 5 wherein the SERRS or SERS surface is a metal surface and the analyte analog portion of the agent is brought into close proximity to the metal SERRS or SERS surface during detection in step (c).

7. A method as claimed in claim 4 wherein the multiple antibodies are cross-specific for the multiple target analytes, and each agent comprises the same analyte analog and wherein the distinctive SERRS or SERS spectrum of each agent is dependent on a distinctive label present in said agent.

8. A method as claimed in claim 1 wherein a full SERRS or SERS spectrum across a range of wavelengths is obtained in step (c).

9. A method as claimed in claim 1 wherein the SERRS or SERS surface is an aggregation of metal colloid particles, wherein the metal is selected from silver, gold or copper.

10. A method as claimed in claim 9 wherein the metal comprises an organic coating selected from the group consisting of citrate; a polyamine and polyphenol.

11. A method as claimed in claim 1 wherein the antibody is immobilised in a glass or plastic capillary tube.

12. A method as claimed in claim 11 wherein multiple antibodies are present in two or more capillary tubes linked together in series.

13. A method as claimed in claim 1 wherein the antibody is immobilised on a bead or microtitre plate.

14. An agent for use in a method as claimed in claim 1, the agent being capable of specifically binding an antibody raised to an analyte and being SERRS or SERS active, wherein said agent comprises an analyte-analog portion and a SERRS or SERS surface-seeking group.

15. An agent as claimed in claim 14 wherein the analyte analog portion is selected from the group consisting of a drug or pharmaceutical or metabolite thereof; an explosive; a pesticide; and an environmental pollutant.

16. An agent as claimed in claim 15 wherein the drug is selected from the group consisting of amphetamines, opiates, benzodiazepines, barbiturates, cannabinoids, cocaine, lysergic acid diethylamide and their metabolites.

17. An agent as claimed in claim 14 wherein the SERRS or SERS spectrum of the agent is dependent on inherent properties of the analyte analog in the agent.

18. An agent as claimed in claim 17 wherein the analyte-analog portion of the agent is derivitised to the surface seeking group either directly or via an azo group.

19. An agent as claimed in claim 18 wherein the agent contains at least one of a chromophore and a fluorophore to enhance the SERRS or SERS activity of the agent.

20. An agent as claimed in claim 19 comprising an azo group.

21. An agent as claimed in claim 14 wherein the agent contains a linking group.

22. An agent as claimed in claim 21 wherein the linking group alters the resonance frequency of the agent.

23. An agent as claimed in claim 22 wherein the linking group is dimethoxyaniline.

24. An agent as claimed in claim 14 wherein the SERRS or SERS surface-seeking group is capable of immobilizing the agent to the SERRS or SERS surface.

25. An agent as claimed in claim 14 wherein the SERRS or SERS surface-seeking group comprises a heterocyclic compound which contains at least two heteroatoms which may be the same or different selected from: nitrogen, sulphur or phosphorous.

26. An agent as claimed in claim 25 wherein the SERRS or SERS surface-seeking group is the benzotriazole group or a derivative thereof.

27. An agent as claimed in claim 14 wherein the SERRS or SERS surface-seeking group comprises a group selected from any one of formulae A1 to A25 as shown in FIG. 6A.

28. An agent as claimed in claim 27 wherein the SERRS or SERS surface-seeking group comprises a group selected from either formula A5 or formula A6 as shown in FIG. 6A.

29. An agent as claimed in claim 14 bound to an antibody.

30. An agent as claimed in claim 14 bound to a SERRS or SERS surface via a SERRS or SERS surface-seeking group.

31. A method as claimed in claim 4, wherein each antibody is immobilised in a glass or plastic capillary tube.

32. A method as claimed in claim 4, wherein each antibody is immobilised on a bead or microtitre plate.

* * * * *